(12) United States Patent
Sampalis

(10) Patent No.: US 10,028,968 B2
(45) Date of Patent: Jul. 24, 2018

(54) NATURAL MARINE SOURCE PHOSPHOLIPIDS COMPRISING POLYUNSATURATED FATTY ACIDS AND THEIR APPLICATIONS

(71) Applicant: AKER BIOMARINE ANTARCTIC AS, Stamsund (NO)

(72) Inventor: Fotini Sampalis, Laval (CA)

(73) Assignee: AKER BIOMARINE ANTARCTIC AS, Stamsund (NO)

( * ) Notice: Subject to any disclaimer, the term of this patent is extended or adjusted under 35 U.S.C. 154(b) by 0 days.

(21) Appl. No.: 15/260,217

(22) Filed: Sep. 8, 2016

(65) Prior Publication Data

US 2017/0216322 A1 Aug. 3, 2017

Related U.S. Application Data

(63) Continuation of application No. 14/528,540, filed on Oct. 30, 2014, now abandoned, which is a continuation of application No. 13/750,663, filed on Jan. 25, 2013, now abandoned, which is a continuation of application No. 13/545,830, filed on Jul. 10, 2012, now Pat. No. 8,383,675, which is a continuation of application No. 13/189,714, filed on Jul. 25, 2011, now Pat. No. 8,278,351, which is a continuation of application No. 10/485,094, filed as application No. PCT/CA02/01185 on Jul. 29, 2002, now Pat. No. 8,030,348.

(60) Provisional application No. 60/307,842, filed on Jul. 27, 2001.

(51) Int. Cl.
| | | |
|---|---|---|
| A61K 31/23 | (2006.01) | |
| A61K 31/661 | (2006.01) | |
| A61K 9/48 | (2006.01) | |
| A61K 31/683 | (2006.01) | |
| A61K 31/685 | (2006.01) | |
| A61K 31/122 | (2006.01) | |
| A61K 9/00 | (2006.01) | |
| A61K 35/612 | (2015.01) | |
| A23J 7/00 | (2006.01) | |
| A23L 33/115 | (2016.01) | |
| A23L 33/00 | (2016.01) | |

(52) U.S. Cl.
CPC .............. *A61K 31/661* (2013.01); *A23J 7/00* (2013.01); *A23L 33/115* (2016.08); *A23L 33/30* (2016.08); *A61K 9/0053* (2013.01); *A61K 9/48* (2013.01); *A61K 31/122* (2013.01); *A61K 31/683* (2013.01); *A61K 31/685* (2013.01); *A61K 35/612* (2013.01); *A23V 2002/00* (2013.01); *Y10S 514/824* (2013.01)

(58) Field of Classification Search
None
See application file for complete search history.

(56) References Cited

U.S. PATENT DOCUMENTS

| | | | |
|---|---|---|---|
| 4,331,695 | A | 5/1982 | Zosel |
| 4,559,234 | A | 12/1985 | Rubin et al. |
| 4,714,571 | A | 12/1987 | Tremblay et al. |
| 4,915,876 | A | 4/1990 | Lindsay |
| 4,963,527 | A | 10/1990 | Bombardelli et al. |
| 5,006,281 | A | 4/1991 | Rubin et al. |
| 5,230,915 | A | 7/1993 | Shahidi et al. |
| 5,425,956 | A | 6/1995 | Shahidi et al. |
| 5,434,183 | A | 7/1995 | Larsson-Backstrom |
| 5,443,852 | A | 8/1995 | Shahidi et al. |
| 6,055,936 | A | 5/2000 | Collin |
| 6,083,536 | A | 7/2000 | Macrides et al. |
| 6,265,450 | B1 | 7/2001 | Asami et al. |
| 6,521,768 | B2 | 2/2003 | Beaudoin |
| 6,713,447 | B2 | 3/2004 | Beaudoin |
| 6,800,299 | B1 | 10/2004 | Beaudoin et al. |
| 7,572,464 | B2 | 8/2009 | Chandler |
| 7,763,717 | B1 | 7/2010 | Jaczynski |
| 8,030,348 | B2 | 10/2011 | Sampalis |
| 8,057,825 | B2 | 11/2011 | Sampalis |
| 8,278,351 | B2 | 10/2012 | Sampalis |
| 8,383,675 | B2 | 2/2013 | Sampalis |
| 8,680,080 | B2 | 3/2014 | Sampalis |
| 2003/0083238 | A1 | 5/2003 | Toda et al. |
| 2011/0104297 | A1 | 5/2011 | Bruheim |
| 2011/0160161 | A1 | 6/2011 | Sampalis et al. |
| 2012/0065172 | A1 | 3/2012 | Sampalis |
| 2012/0214771 | A1 | 8/2012 | Sampalis |
| 2012/0277196 | A1 | 11/2012 | Sampalis |
| 2013/0202689 | A1 | 8/2013 | Sampalis |
| 2015/0038469 | A1 | 2/2015 | Sampalis |
| 2015/0164927 | A1 | 6/2015 | Sampalis |

FOREIGN PATENT DOCUMENTS

| | | |
|---|---|---|
| AU | 671329 B | 8/1996 |
| CA | 1098900 A | 4/1981 |
| CA | 2115571 A1 | 12/1993 |
| CA | 2251265 A1 | 4/2000 |

(Continued)

OTHER PUBLICATIONS

U.S. Appl. No. 60/298,383, filed Jun. 18, 2001, Sampalis.

(Continued)

*Primary Examiner* — Savitha M Rao
*Assistant Examiner* — Gregg Polansky
(74) *Attorney, Agent, or Firm* — Casimir Jones S.C.; J. Mitchell Jones

(57) ABSTRACT

A phospholipid extract from a marine or aquatic biomass possesses therapeutic properties. The phospholipid extract comprises a variety of phospholipids, fatty acid, metals and a novel flavonoid.

7 Claims, 4 Drawing Sheets

(56) References Cited

FOREIGN PATENT DOCUMENTS

| | | |
|---|---|---|
| CA | 2362663 A1 | 6/2001 |
| EP | 0275005 A2 | 7/1988 |
| EP | 0209037 B1 | 2/1990 |
| EP | 0554283 | 5/1992 |
| EP | 0507363 B1 | 5/1993 |
| EP | 0275224 B1 | 7/1993 |
| EP | 0609078 A1 | 8/1994 |
| EP | 0209038 B2 | 3/1996 |
| EP | 0732378 A2 | 9/1996 |
| EP | 0773283 B1 | 7/1999 |
| ES | 2088750 B1 | 3/1997 |
| JP | 51-76467 | 7/1976 |
| JP | 53-112195 | 9/1978 |
| JP | 55-23949 A | 2/1980 |
| JP | 59-196032 A | 11/1984 |
| JP | 60-35057 A | 2/1985 |
| JP | 60-153779 A | 8/1985 |
| JP | 63-23819 | 7/1986 |
| JP | 63-295698 | 12/1988 |
| JP | 64-50890 A | 2/1989 |
| JP | 2-167055 | 6/1990 |
| JP | 2-215351 A | 8/1990 |
| JP | 4-57853 A | 2/1992 |
| JP | 4-273817 | 9/1992 |
| JP | 6-237703 | 8/1994 |
| JP | 8-198754 A | 8/1996 |
| JP | 8-231391 | 9/1996 |
| JP | 8-302382 A | 11/1996 |
| JP | 2909508 B2 | 6/1999 |
| JP | 2000-60432 A | 2/2000 |
| KR | 2002037140 | 5/2002 |
| NO | 147365 B | 12/1982 |
| WO | WO 84/01715 A1 | 5/1984 |
| WO | WO 92/21335 A1 | 12/1992 |
| WO | WO 96/37200 A1 | 11/1996 |
| WO | WO 97/39759 A2 | 10/1997 |
| WO | WO 99/64547 A1 | 12/1999 |
| WO | WO 00/23546 A1 | 4/2000 |
| WO | WO 00/44862 A1 | 8/2000 |
| WO | WO 02/092540 | 11/2002 |
| WO | WO 02/102394 | 12/2002 |

OTHER PUBLICATIONS

U.S. Appl. No. 60/307,842, filed Jul. 27, 2001, Sampalis.
International Search Report for International Application No. PCT/CA2002/001185, dated Feb. 20, 2003, 5 pages.
Declaration of Earl L. White Under 37 C.F.R. 1.132, filed in U.S. Appl. No. 10/485,094, U.S. Pat. No. 8,030,348, dated May 31, 2011, 32 pages.
Office Action for U.S. Appl. No. 13/189,714, now U.S. Pat. No. 8,278,351, dated Jan. 5, 2012, 13 pages.
Amendment/Response to Office Action for U.S. Appl. No. 13/189,714, now U.S. Pat. No. 8,278,351, filed Apr. 2, 2012, 43 pages.
Declaration of Fereidoon Shahidi Under 37 C.F.R. 1.132, filed in U.S. Appl. No. 13/189,714, dated Mar. 29, 2012, 160 pages.
Declaration of Jacek Jaczynski Under 37 C.F.R. 1.132, filed in U.S. Appl. No. 13/189,714, dated Mar. 29, 2012, 221 pages.
Supplemental Declaration of Earl L. White, filed in U.S. Appl. No. 13/189,714, dated Mar. 29, 2012, 19 pages.
Declaration of Faustinus Yeboah Under 37 C.F.R. 1.132, filed in U.S. Appl. No. 13/189,714, dated Mar. 16, 2012, 80 pages.
ACS Chemical Registry, "4H-1-Benzopyran-4-one, 2-(3,4-dihydroxyphenyl)-6-8-di-β-D-glucopyranosyl-5,7-dihydroxy-", Nov. 16, 1984, 1 page.
"Aglycon (aglycone)" Definition, IUPAC Compendium of Chemical Terminology, The Gold Book, Second Edition, Blackwell Science, 1997 [ISBN 0865426848], 3 pages.
Letter to Office of Food Additive Safety (HFS-255) from Madhu Soni, Re: Notification of GRAS Determination for Krill Oil, Dec. 14, 2010, 45 pages.
Amate et al., "Feeding Infant Piglets Formula with Long-Chain Polyunsaturated Fatty Acids as Triacylglycerols or Phospholipids Influences the Distribution of these Fatty Acids in Plasma Lipoprotein Fractions," J Nutr. 131:1250-1255 (2001).
Araki et al., "Positional Distribution of Fatty Acids in Glycerolipids of the Marine Red Alga, Porphyra yezoensis," Plant Cell Physiol. 28(5):761-766 (1987).
Aureli et al., "Aging brain: effect of acetyl-L-carnitine treatment on rat brain energy and phospholipid metabolism. A study by 31P and 1H NMR spectroscopy," Brain Research 526(1):108-112 (1990).
Balassa et al., "Microencapsulation in the Food Industry," Critical Reviews in Food Technology, 2(2):245-265 (1971).
Bandyukova, V. A. et al., "Natural Flavonoid C-Glycosides," Chemistry of Natural Compounds, vol. 17, No. 1 Jan.-Feb. 1981, Translated from Khimiya Prirodnykh Soedinenii, No. 1, pp. 5-24 (Jan.-Feb. 1981).
Barak et al., "Inositol Treatment of Alzheimer's Disease: A Double Blind, Cross-Over Placebo Controlled Trial," Prog. Neuro-Psychopharmacol. Biol. Psychiat. 20:729-735 (1996).
Barkai et al., "Reduced Myo-Inositol Levels in Cerebrospinal Fluid from Patients with Affective Disorder," Biol. Psychiatry 13:65-72 (1978).
Basile et al., "Antibacterial activity of pure flavonoids isolated from mosses," Phytochemistry 52(8):1479-1482 (1999).
Bast et al., "Interplay between lipoic acid and glutathione in the protection against microsomal lipid peroxidation," Biochem. Biophys. Acta. 963:558-561 (1988).
Bell et al., "Molecular Species Composition of the Major Diacyl Glycerophospholipids from Muscle, Liver, Retina and Brain of Cod (Gadus morhua)," Lipids, 26(8):565-573 (1991).
Bell, M. V., "Molecular Species Analysis of Phosphoglycerides from the Ripe Roes of Cod (Gadus morhua)," Lipids, 24(7):585-588 (1989).
Bell, M. V. et al., "Molecular Species Composition of Phosphatidylcholine from Crypthecodinium cohnii in Relation to Growth Temperature," Lipids 25(2):115-118 (1990).
Benjamin et al., "Double-blind, placebo-controlled, crossover trial of inositol treatment for panic disorder," Am. J. Psychiatry 15:1084-1086 (1995).
Bergelson, L. D. (ed.), "Preparative extraction of lipids from natural sources," Chapter 1.1 in Lipid Biochemical Preparations, Elsevier/North-Holland Biomedical Press, Amsterdam-New York-Oxford, pp. 1-13 (1980), 28 pages.
Berkow, R. et al. (eds.), "Generalized Cardiovascular Disorders," Chapter 24 In: The Merck Manual of Diagnosis and Therapy, Sixteenth Edition, Merck Research Laboratories, Rahway, NJ, USA, pp. 409-431 (1992).
Birchall et al., "Aluminium, Chemical Physiology, and Alzheimer's Disease," Lancet 29:1008-1010 (1988).
Bottino et al., "Resistance of Certain Longchain Polyunsaturated Fatty Acids of Marine Oils to Pancreatic Lipase Hydrolysis" Lipids 2, 489-93 (1967).
Bowyer et al., "The Determination of the Fatty Acid Composition of Serum Lipids Separated by Thin-Layer Chromatography; and a Comparison with Column Chromatography," Biochim. Biophys. Acta 70:423-431 (1963).
Bridges et al., "Determination of Digestibility, Tissue Deposition, and Metabolism of the Omega-3 Fatty Acid Content of Krill Protein Concentrate in Growing Rats" J Agric Food Chem 58: 2830-7 (2010).
Buchi, Operation Manual Rotavapor R-220, Buchi Labortechnik AG (1999-2001), 50 pages.
Buda, C. et al., "Structural order of membranes and composition of phospholipids in fish brain cells during thermal acclimatization," Proc. Natl. Acad. Sci. USA, 91:8234-8238 (Aug. 1994).
Bunea et al., "Evaluation of the Effects of Neptune Krill Oil on the Clinical Course of Hyperlipidemia" Altern Med Rev 9: 420-28 (2004).
Burgess et al., "Long-chain polyunsaturated fatty acids in children with attention-deficit hyperactivity disorder," Am. J. Clin. Nutr. 71(suppl):327S-330S (2000).

(56) References Cited

OTHER PUBLICATIONS

Caprioli et al., "Age-Dependent Deficits in Radial Maze Performance in the Rat: Effect of Chronic Treatment with Acetyl-L-Carnitine," Prog. Neuro-Psychopharmacol. Biol, Psychiat. 14(3):359-369 (1990).
Carell et al., "A Novel Procedure for the Synthesis of Libraries Containing Small Organic Molecules," Angew. Chem. Int. Ed. Engl. 33(20):2059-2061 (1994).
Carell et al., "A Solution-Phase Screening Procedure for the Isolation of Active Compounds from a Library of Molecules," Angew. Chem. Int. Ed. Engl. 33(20):2061-2064 (1994).
Carnielli et al., "Intestinal absorption of long-chain polyunsaturated fatty acids in preterm infants fed breast milk or formula," Am J Clin Nutr 67:97-103 (1998).
Cenacchi et al., "Cognitive decline in the elderly: A double-blind, placebo-controlled multicenter study on efficacy of phosphatidylserine administration," Aging Clin. Exp. Res. 5:123-133 (1993).
Chandrasekar et al., "Tissue specific regulation of transforming growth factor beta by Omega-3 lipid-rich krill oil in autoimmune murine lupus," Nutr. Res. 16(3):489-503 (1996).
Chateau et al., "Dimethyl sulfoxide-induced apoptosis in human leukemic U937 cells," Anal. Cell. Pathol. 10:75-84 (1996).
Cheng et al., "Huperzine A, a novel promising acetylcholinesterase inhibitor," NeuroReport 8:97-101 (1996).
Christensen et al., "Lymphatic absorption of n-3 polyunsaturated fatty acids from marine oils with different intramolecular fatty acid distributions," Biochim. Biophys. Acta 1215:198-204 (1994).
Church et al., "Spectrophotometric Assay Using o-Phthaldialdehyde for Determination of Proteolysis in Milk and Isolated Milk Proteins," J. Dairy Sci. 66:1219-1227 (1983).
Cohen et al., "Brain Choline Uptake and Cognitive Function in Middle Age," Biol. Psych . 41:90S, Abstract No. 307 (1997).
Cohen et al., "Inositol has behavioral effects with adaptation after chronic administration," J. Neural Transm. 104:299-305 (1997).
Colodny et al., "Inositol—Clinical Applications for Exogenous Use," Altern. Med. Rev. 3(6):432-447 (1998).
Crook et al., "Effects of phosphatidylserine in age-associated memory impairment," Neurology 41:644-649 (1991).
Dawson et al., "8 Lipids and long-chain fatty acids," pp. 181-184, in Data for Biochemical Research, 3rd Edition (1986).
Delwaide et al., "Double-blind randomized controlled study of phosphatidylserine in senile demented patients," Acta Neurol. Scand. 73:136-140 (1986).
Deutch, "Menstrual pain in Danish women correlated with low n-3 polyunsaturated fatty acid intake," Eur. J. Clin. Nutr. 49(7):508-516 (1995).
Devasagayam et al., "Prevention of Singlet Oxygen-Induced DNA Damage by Lipoate," Chem.-Biol. Interactions 86:79-92 (1993).
Edwards et al., "Omega-3 polyunsaturated fatty acid levels in the diet and in red blood cell membranes of depressed patients," J. Affect. Disord. 48(2-3):149-155 (1998).
Eichberg, J., "Lecithin-Its Manufacture and Use in the Fat and Oil Industry," Oil & Soap, pp. 51-54 (Mar. 1939).
Elliott et al., Current Trends in Quantitative Proteomics. J. Mass. Spectrom., 44 (12): 1637-1660 (2009).
Estiarte et al., "Free-air CO2 enrichment of wheat: leaf flavonoid concentration throughout the growth cycle," Physiologia Plantarum 105(3):423-433 (1999).
EWG's Skin Deep Cosmetics Database, "Glycolix Elite Treatment Pads 10% (2010 formulation)," [online], [Retrieved from the Internet: Aug. 29, 2013], <URL:http://www.ewg.org/skindeep/product/40396/glycolix_elite_treatment_pads_10%25_%282 . . . >, 3 pages.
Farkas, T., "Composition and Physical State of Phospholipids in Calanoid Copepods from India and Norway," Lipids, 23(6):619-622 (1988).
Folch et al., "A Simple Method for the Isolation and Purification of Total Lipides from Animal Tissues," J. Biol. Chem. 226:497-509 (1957).

Fricke et al., "Lipid, Sterol and Fatty Acid Composition of Antarctic Krill," Lipids, 19(11):821-827 (1984).
Fujita, T., "Development of technology for recovery of valuable substances (astaxanthin) from krill," Chapter 6 In: Research & Development for Processing and Usage of Marine Products, Comprehensive Report, Library of the Ministry of Agriculture, Foresty and Fisheries, Fisheries Agency Research Department, Research Division, pp. 273-307 (Mar. 1985).
Gadaleta et al., "Mitochondrial DNA Transcription and Translation in Aged Rat. Effect of Acetyl-L-carnitine," Ann. N.Y. Acad. Sci. 717:150-160 (1994).
Ghirardi et al., "Effect of Acetyl-L-Carnitine Chronic Treatment on Discrimination Models in Aged Rats," Physiol. Behav. 44(6):769-773 (1988).
Gigliotti et al., "Extraction and Characterisation of Lipids from Antarctic Krill (Euphausia superba)" Food Chemistry 125(3): 1028-1036 (Apr. 2011).
Gill et al., "Calcium signalling mechanisms in endoplasmic reticulum activated by inositol 1,4,5-triphosphate and GTP," Cell Calcium 10:363-374 (1989).
Gordeev et al., "Fatty Acid Composition of the Main Phospholipids of the Antarctic Krill Euphausia superba," Scientific Research Laboratory of Biologically Active Substances of Hydrobionts, USSR Ministry of Health, Moscow, translated from Khimiya Prirodnykh Soedinenii, No. 2, 181-187 (Mar.-Apr. 1990), original article submitted Apr. 17, 1989.
Grit et al., "Hydrolysis of Phosphatidylcholine in Aqueous Liposome Dispersions," Int. J. Pharmaceutics, 50:1-6 (1989).
Hanahan et al., "Complex Lipids," Ann. Rev. Biochem. 32:215-240 (1963).
Henderson, R. J. et al., "Lipid Composition of the Pineal Organ from Rainbow Trout (*Oncorhynchus mykiss*)," Lipids 29(5):311-317 (1994).
Herman et al., "The Influence of Free Fatty Acid Formation on the pH of Phospholipid-Stabilized Triglyceride Emulsions," Pharmaceutical Research, 10(5):774-776 (1993).
Hernell et al., "Does the Bile Salt-Stimulated Lipase of Human Milk Have a Role in the Use of the Milk Long-Chain Polyunsaturated Fatty Acids?," J Pediatr Gastroenterol Nutr 16: 426-31 (1993).
High Beam Research, "Neptune Technologies IPO Warmly Received in Cool Financial Climate," Canadian Corporate News [online], [Retrieved from the Internet: Feb. 22, 2008], <URL:http://www.highbeam.com/DocPrint.aspx?DocId=1G1:75343660>, (Jun. 7, 2001), 3 pages.
Hong et al., "Novel Docosatrienes and 17S-resolvings Generated from Docosahexaenoic Acid in Murine Brain, Human Blood, and Glial Cells. Autacoids in Anti-Inflammation" J Biol Chem 278(17): 14677-87 (2003).
Hosokawa, M. et al., "Conversion to Docosahexaenoic Acid-Containing Phosphatidylserine from Squid Skin Lecithin by Phospholipase D-Mediated Transphosphatidylation," J. Agric. Food Chem. 48(10):4550-4554 (2000).
Houghten et al., "The Use of Synthetic Peptide Combinatorial Libraries for the Identification of Bioactive Peptides," BioTechniques 13(3):412-421 (1992).
Hughes et al., "Determination of Carryover and Contamination for Mass Spectrometry-Based Chromatographic Assay," The AAPS Journal 2007;9(3) Article 42 (http://www.aapsj.org).
Ikeda et al., "Effects of Long-Term Feeding of Marine Oils with Different Positional Distribution of Eicosapentaenoic and Docosahexaenoic Acids on Lipid Metabolism, Eicosanoid Production, and Platelet Aggregation in Hypercholesterolemic Rats," Lipids, 33(9):897-904 (1998).
Imperato et al., "Acetyl-L-carnitine enhances acetylcholine release in the striatum and hippocampus of awake freely moving rats,"Neurosci. Lett. 107(1-3):251-255 (1989).
In the Matter of Certain Omega-3 Extracts from Marine or Aquatic Biomass and Products Containing the Same, United States International Trade Commission, "Expert Witness Report of Theodore F. Welch, Ph.D. Regarding Public Accessibility of Certain References," Investigation No. 337-TA-877, filed Sep. 16, 2013, 60 pages.

(56) References Cited

OTHER PUBLICATIONS

Itano Refrigerated Food Co., Ltd., Bio & High Technology Announcement and Natural Astaxanthin & Krill Lecithin, pp. 1-16 (Jan. 16, 1994).
Iwashina, "The Structure and Distribution of the Flavonoids in Plants," J. Plant Res. 113:287-299 (2000).
Jay, M., "C-Glycosylflavonoids," Chapter 3 In: The Flavonoids: Advances in Research Since 1986, First Edition, Harborne, J.B. (ed.), Chapman & Hall, London (1994), pp. 57-93.
Johnson, L. A. et al., "Comparison of Alternative Solvents for Oil Extraction," JAOCS, 60(2):229-242 (Feb. 1983).
Kagan et al., "Dihydrolipoic Acid—A Universal Antioxidant Both in the Membrane and in the Aqueous Phase. Reduction of Peroxyl, Ascorbyl and chromanoxyl Radicals," Biochem. Pharmacol 44:1637-1649 (1992).
Kalmijn et al., "Polyunsaturated Fatty Acids, Antioxidants, and Cognitive Function in Very Old Men," Am. J. Epidemiol. 145(1):33-41 (1997).
Kalmijn et al., "Dietary Fat Intake and the Risk of Incident Dementia in the Rotterdam Study," Ann. Neurol. 42:776-782 (1997).
Kassis et al., "Characterization of Lipids and Antioxidant Capacity of Novel Nutraceutical Egg Products Developed with Omega-2-Rich Oils," J Sci Food Agr 92(1):66-73 (2012).
Kawakami et al., "The Rationale for E2020 as a Potent Acetylcholinesterase Inhibitor," Bioorg. Med. Chem. 4:1429-1446 (1996).
KEGG Compound: C10102, Lucenin-2; Luteolin 6,8-di-C-glucoside [online], [Retrieved from the Internet on Oct. 4, 2011], <URL:http://www.genome.jp/dbget-bin/www_bget?cpd:C10102>, 1 page.
Kidd, "Phosphatidylcholine: A Superior Protectant Against Liver Damage," Alt. Med. Rev. 1:258-274 (1996).
Kitamura et al., "Inhibition of myo-inositol transport causes acute renal failure with selective medullary injury in the rat," Kidney Int. 53:146-153 (1998).
Knopman et al., "Long-term tacrine (Cognex) treatment: Effects on nursing home placement and mortality, tacrine study group," Neurology 47:166-167 (1996).
Kojima et al., "Different Changes in Expression and Function of Connexin 26 and Connexin 32 During DNA Synthesis and Redifferentiation in Primary Rat Hepatocytes Using a DMSO Culture System," Hepatology 26(3):585-597 (1997).
Kristensen et al., "Dietary supplementation with n-3 polyunsaturated fatty acids and human platelet function: a review with particular emphasis on implications for cardiovascular disease," J. Intern. Med. 225(Suppl. 1):141-150 (1989).
Kuroda et al., "Comparison of Hypocholesterolemic Effect among Three Phospholipids Containing Different Fatty Acid and the Related Oils in Rats," Jpn. J. Nutr., 48(5):213-220 (1990).
Lam, "Application of combinatorial library methods in cancer research and drug discovery," Anti-Cancer Drug Design 12:145-167 (1997).
Le Grandois et al., "Investigation of Natural Phosphatidylholine Sources: Separation and Identification by Liquid Chromatography Electrospray Ionization-Tandem Mass Spectrometry (LC-ESI-MS2) of Molecular Species," J. Agric. Food Chem., 57:6014-6020 (2009).
Lemaitre-Delaunay et al., "Blood compartmental metabolism of docosahexaenoic 207. acid (DHA) in humans after ingestion of a single dose of [13C]DHA in phosphatidylcholine," Journal of Lipid Research, 40:1867-1874 (1999).
Levine et al., "Double-blind, controlled trial of inositol treatment of depression," Am. J. Psychiatr. 152(5):792-794 (May 1995).
Levine et al., "Follow-up and Relapse Analysis of an Inositol Study of Depression," Isr. J. Psychiatry Relat. Sci., 32(1):14-21 (1995).
Levine et al., "Inositol treatment raises CSF inositol levels," Brain Research, 627:168-169 (1993).
Levine, J., "Controlled trials of inositol in psychiatry," Eur. Neuropsychopharmacol. 7:147-155 (1997).

Levy et al., "The novel Flavonoid Chemistry and Phylogenetic Origin of Phlox Floridana," Evolution 29:487-499 (Sep. 1975).
Lin et al., "Effect of Dietary N-3 Fatty Acids Upon the Phospholipid Molecular Species of the Monkey Retina," Invest Ophthalmol Vis Sci., 35:794-803 (1994).
Makuta et al., "Effects of EPA and Use in Health Foods," Japan Food Science, 25(1):29-35 (1986).
Markham et al., "Luteolin 7-Glucuronide-3'-Mono(trans)ferulylglucoside and other Unusual Flavonoids in the Aquatic Liverwort Complex, Riccia fluitans," Phytochemistry 17:1601-1604 (1978).
Masson et al., "Influence of hazelnut oil phospholipids on the skin moisturizing effect of a cosmetic einulsion," International Journal of Cosmetic Science, 12:243-251 (1990).
Mattson et al., "The Digestion and Absorption of Triglycerides" J Biol Chem 239:2772-7 (1964).
McCormick et al., "The Flavonoids of Passiflora Sexflora," J. Nat. Prod. 45(6):782 (1982).
Medina et al., "13C Nuclear magnetic resonance monitoring of free fatty acid release after fish thermal processing" J. Amer. Oil Chem. Soc., 71(5):479-482 (1994).
Mills et al., "Dietary N-6 and N-3 Fatty Acids and Salt-induced Hypertension in the Borderline Hypertensive Rat," Lipids 24(1):17-24 (1989).
Mohr et al., "Treatment of Alzheimer's Disease with Sabeluzole: Functional and Structural Correlates," Clin. Neuropharmacol. 20:338-345 (1997) (Abstract only).
Morgan et al., "Fatty Acid Balance Studies in Term Infants Fed Formula Milk Containing Long-Chain Polyunsaturated Fatty Acids" Acta Paediatr 87: 136-42 (1998).
Mori et al., "Purified eicosapentaenoic and docosahexaenoic acids have differential effects on serum lipids and lipoproteins, LDL particle size, glucose, and insulin in mildly hyperlipidemic men," Am. J. Clin. Nutr. 71:1085-1094 (2000).
Navarra et al., pp. 134, 141-142 in Encyclopedia of Vitamins, Minerals and Supplements (1996).
Natural Nutritionals, Designs for Health—Neptune Krill Oil—120 Gels [online], [Retrieved from the Internet on Jan. 23, 2008], <URL: http://www.naturalnutritionals.com/kril4.html>, 2 pages.
Neptune Technologies & Bioressources Inc., Amended Preliminary Prospectus, Mar. 12, 2001, 73 pages.
Neptune Technologies & Bioressources Inc., Final Prospectus, May 11, 2001, 81 pages.
Neptune Technologies & Bioressources Inc., "Neptune Technologies & Bioressources Soon to Obtain a Major Patent in Over 30 Countries," Press Release Jun. 14, 2001 [online], [Retrieved from the Internet on May 24, 2012], <URL:http://cnrp.ccnmatthews.com/news/releases/show.jsp?action=showRelease&actionFor . . . >, 2 pages.
Newberne et al., "Lipotropes, Immunocompetence, and Cancer," Cancer Res. 43(Suppl.):2426s-2434s (1983).
O'Doherty et al., "Role of Luminal Lecithin in Intestinal Fat Absorption," Lipids 8:249-255 (1973).
Pages from www.seakrill.com with publications (computer translations from Spanish to English) (Sep. 1997 and Oct. 1999), 7 pages.
Paradies et al., "Carnitine-acylcarnitine translocase activity in cardiac mitochondria from aged rats: the effect of acetyl-L-carnitine," Mech. Aging Develop. 84(2):103-112 (1995).
Parthasarathy et al., "Biochemical and Molecular Properties of Lithium-Sensitive Myo-Inositol Monophosphatase," Life Sci. 54(16):1127-1142 (1994).
Prados et al., "Actin, Tropomyosin and α-Actinin as Markers of Differentiation in Human Rhabdomyosarcoma Cell Lines Induced with Dimethyl Sulfoxide," Cell. Mol. Biol. 39(5):525-536 (1993).
Prentice et al., "Nerve growth factor-induced changes in neural cell adhesion molecule (N-CAM) in PC12 cells," EMBO J. 6(7):1859-1863 (1987).
Raa et al., "Isolation of astaxanthin from crayfish or shrimp waste for use as a coloring agent in fish feed," Chem. Abstracts 98:177859m (1983).
Rao et al., "Phytochemical Investigation on Leaves of Rhynchosia Densiflora," Indian J. Nat. Prod. 14(1):20-22 (1998).

(56) References Cited

OTHER PUBLICATIONS

Roberson, E. D. et al., "100 Years and Counting: Prospects for Defeating Alzheimer's Disease," Science, 314:781-784 (Nov. 3, 2006).
Rogers et al., "MaxEPA Fish Oil Enhances Cholesterol-induced Intimal Foam Cell Formation in Rabbits," Am. J. Pathol. 137(4):945-951 (1990).
Rogers et al., "The Efficacy and Safety of Donepezil in Patients with Alzheimer's Disease: Results of a US Multicentre, Randomized, Double-Blind, Placebo-Controlled Trial," Dementia 7:293-303 (1996) (Abstract only).
Sampalis et al., "Evaluation of the Effects of Neptune Krill Oil™ on the Management of Premenstrual Syndrome and Dysmenorrheal," Altern Med Rev 8: 171-9 (2003).
Sargent, "Fish oils and human diet," Br. J. Nutr. 78(Suppl. 1):S5-S13 (1997).
Saynor et al., "Changes in Blood Lipids and Fibrinogen with a Note on Safety in a Long Term Study on the Effects of n-3 Fatty Acids in Subjects Receiving Fish Oil Supplements and Followed for Seven Years," Lipids 27(7):533-538 (1992).
Schmidt, M. A., "The Newest Brain Foods: Krill Oil and Red Palm Oil," Chapter 15 In: Brain-Building Nutrition. The Healing Power of Fats & Oils, Frog Ltd., Berkeley, CA (1997), pp. 208-217.
Schneider et al., "Potential Role for Estrogen Replacement in the Treatment of Alzheimer's Dementia," Am. J. Med. 103(3A):46S-50S (1997).
Seidman et al., "Biologic Activity of Mitochondrial Metabolites on Aging and Age-Related Hearing Loss," Am. J. Otol. 21:161-167 (2000).
Seidman, "Polyunsaturated Phosphatidylcholine in NT Factor™ Improves Mitochondrial Function, Auditory Sensitivity and May Slow Some Aspects of the Aging Process," Anti-Aging Medical News, pp. 5, 16-19 (2001).
Serbinova et al., "Thioctic Acid Protects Against Ischemia-Reperfusion Injury in the Isolated Perfused Langendorff Heart," Free Rad. Res. Commun. 17:49-58 (1992).
Sharaf, "Isoscutellarein 8-O-(6"-trans-p-coumaroyl)-β-D-glucoside from Stachys aegyptiaca," Fitoterapia 69(4):355-357 (1998).
Simopoulos, "Omega-3 fatty acids in health and disease and in growth and development," Am. J. Clin. Nutr. 54:438-463 (1991).
Simopoulos, "Omega-3 Fatty Acids in Inflammation and Autoimmune Diseases," J Am Coll Nutr 21(6):495-505 (2002).
Singh, R. P., "Heating and Cooling Processes for Foods," Chapter 5 In: Handbook of Food Engineering, Heldman et al. (eds.), New York, NY: Marcel Dekker, pp. 247-259 (1992).
Singh, R. P. et al., "Introduction to Food Engineering" (3rd ed.), New York, NY: Academic Press, pp. 222-227 (2008).
Sjölander et al., "Integrated Fluid Handling System for Biomolecular Interaction Analysis," Anal. Chem. 63(29):2338-2345 (1991).
St. Jean, P., "Krill oil production according to the Beaudoin patent," Neptune Technologies & Bioresources, Report R & D Activities in Nov. 2009, 2 pages.
Stoll et al., "Omega-3 fatty acids and bipolar disorder: a review," Prostagland. Leukotrienes Essent. Fatty Acids 60(5&6):329-337 (1999).
Suzuki et al., "The utilization of Antarctic krill for human food," Food Rev. Int. 6(1):119-147 (1990).
Suzuki et al., "α-Lipoic acid is a potent inhibitor of NF-kB activation in human T cells," Biochem. Biophys. Res. Commun. 189:1709-1715 (1992) (Abstract only).
Szabo et al., "Surface plasmon resonance and its use in biomolecular interaction analysis (BIA)," Curr. Opin. Struct. Biol. 5:699-705 (1995).
Takahashi et al., "Compositional Changes in Molecular Species ofFish Muscle PhosphatidylcholineDuring Storage," Bull. Fac. Fish. Hokkaido Univ. 37(1):80-84 (1986).
Takahashi et al., "Molecular Species ofFish Muscle Lecithin," Bulletin of the Japanese Society of Scientific Fisheries 48(12):1803-1814 (1982).
Takahashi et al., "Prediction of Relative Retention Value of the Individual Molecular Species of Diacyl Glycerolipid on High Performance Liquid Chromatography," Bull. Fac. Fish. Hokkaido Univ. 38(4):398-404 (1987).
Tanaka, "Biosynthesis of 1 ,2-dieicosapentaenoyl-sn-glycero-3-phosphocholine in Caenorhabditis elegans," Eur. J. Biochem., 263:189-194 (1999).
Tocher, D. R., "Glycerophospholipid Metabolism," Chapter 6 in Biochemistry and Molecular Biology of Fishes, Hochachka and Mommsen (eds.), vol. 4 (1995), 119 pages.
Tokunaga et al., "Formation of Dimethyl Sulfide in Antarctic Krill," Bull Jpn. Soc. Sci. Fisheries 43(10):1209-1217 (1977).
Tou et al., "Krill for Human Consumption: Nutritional Value and Potential Health Benefits," Nutr Rev 65(2):63-77 (2007).
Trubiani et al., "The c-myc gene regulates the polyamine pathway in DMSO-induced apoptosis," Cell Prolif., 32:119-129 (1999).
True Health Talk Show, Edited Transcript, "Dr. Tina Sampalis on Neptune Krill Oil," Interview by Tom Valentine (2005), [online], [Retrieved from the Internet on Feb. 29, 2008], <URL:http://www.dilesta.com/Tina.htm>, 13 pages.
Tso et al., "Evidence for Separate Pathways of Chylomicron and Very Low-Density Lipoprotein Assembly and Transport by Rat Small Intestine," Am J Physiol., 247:G599-G610 (1984).
U.S. Food and Drug Administration, Guide to Nutrition Labeling and Education Act (NLEA) Requirements—Attachment 6-8 [online], [Retrieved from the Internet on Mar. 16, 2012], <URL: http://www.fda.gov/ICECI/Inspections/InspectionGuides/ucm114098.htm>, 4 pages.
Ulven et al., "Metabolic Effects of Krill Oil are Essentially Similar to Those of Fish Oil But at Lower Dose of EPA and DHA, in Healthly Volunteers," Lipids, 46:37-46 (2011).
Vadnal et al., "Role of Inositol in the Treatment of Psychiatric Disorders. Basic and Clinical Aspects," CNS Drugs 7:6-16 (1997).
van Dyck et al., "The acetylcholine releaser linopirdine increases parietal regional cerebral blood flow in Alzheimer's disease," Psychopharmacology 132:217-226 (1997).
Voirin et al., "Separation of Flavone C-Glycosides and Qualitative Analysis of Passiflora incarnata L. by Capillary Zone Electrophoresis," Phytochem. Anal., 11:90-98 (2000).
Watanabe et al., "Effective Components in Cuttlefish Meal and Raw Krill for Improvement of Quality of Red Seabream Pagrus major Eggs," Nippon Suisan Gakkaishi, 57(4):681-694 (1991).
WHO News and Activities, "Use of DDT in vector control," Bulletin of the World Health Organization, 73(4):547-551 (1995).
Wiegand et al., "Phospholipid Molecular Species of Frog Rod Outer Segment Membranes," Exp. Eye Res. 37(2):159-173 (1983).
Winther et al., "Elucidation of Phosphatidylcholine Composition in Krill Oil Extracted from Euphausia superba Lipids," 46(1):25-36 (2011).
Yamaguchi et al., "Supercritical Carbon Dioxide Extraction of Oils from Antarctic Krill," J. Agric. Food Chem., 34:904-907 (1986).
Yarochkin et al., "Technochemical Characteristics of the Canned Food 'Natural Antarctic Krill Meat' and Its Food Value," Moscow Voprosy Pitaniya in Russian No. 2, Mar.-Apr. 1985 (manuscript received Mar. 30, 1984), pp. 69-72.
Yongmanitchai et al., "Positional distribution of fatty acids, and molecular species of polar lipids, in the diatom Phaeodactylum tricornutum," J. Gen. Microbiol., 139:465-472 (1993).
Youdim et al., "Essential fatty acids and the brain: possible health implications," Int. J. Devl. Neuroscience 18(4-5):383-399 (2000).
Aker Biomarine's Statement of Grounds of Opposition and Particulars Relating to Each Ground, Australian Patent Application No. 2002322233, dated Apr. 22, 2009, 19 pages.
Notice of Opposition to European Patent No. 1417211 submittted by Aker Biomarine ASA, filed Feb. 29, 2008, 32 pages.
Experimental Report on Flavonoid Analysis by Professor Andersen submitted by Aker Biomarine ASA in support of it's Notice of Opposition to European Patent No. 1417211, filed Feb. 29, 2008, 14 pages.
Notice of Opposition to European Patent No. 1417211 submittted by Enzymotec Ltd., filed Feb. 29, 2008, 21 pages.
Decision of Opposition Board Revoking European Patent No. 1417211, filed Dec. 30, 2009, 34 pages.

(56) References Cited

OTHER PUBLICATIONS

Letter to Dorit Plat—Enzymotec Ltd. from Igal Gozlan, Tami-IMI Institute for Research & Development, Re: Figure 4 of European Patent No. 1417211, dated Jan. 14, 2008, 17 pages.
Complaint filed by *Neptune Technologies & Bioressources, Inc., Neptune Technologies & Bioressources, Inc.* v. *Aker Biomarine ASA et al.*, Case No. 1:11-cv-00894 (GMS), United States District Court for the District of Delaware, filed Oct. 4, 2011, 8 pages.
Defendants *Aker Biomarine Antarctic USA Inc. and Schiff Nutrition International, Inc.'s Answer, Affirmative Defenses, Counterclaims and Jury Demand, Neptune Technologies & Bioressources, Inc.* v. *Aker Biomarine ASA et al.*, Case No. 1:11-cv-00894 (GMS), United States District Court for the District of Delaware, filed Dec. 19, 2011, 75 pages.
Complaint filed by *Neptune Technologies & Bioressources, Inc., Neptune Technologies & Bioressources, Inc.* v. *Enzymotec Limited et al.*, Case No. 1:11-cv-00895 (GMS), United States District Court for the District of Delaware, filed Oct. 4, 2011, 49 pages.
Answer of Defendant *Enzymotec USA, Inc., Neptune Technologies & Bioressources, Inc.* v. *Enzymotec Limited et al.*, Case No. 1:11-cv-00895 (GMS), United States District Court for the District of Delaware, filed Dec. 30, 2011, 39 pages.
Answer of Defendant *Mercola.com Health Resources LLC, Neptune Technologies & Bioressources, Inc.* v. *Enzymotec Limited et al.*, Case No. 1:11-cv-00895 (GMS), United States District Court for the District of Delaware, filed Dec. 30, 2011, 38 pages.
Inter Partes Reexamination of U.S. Pat. No. 8,030,348, Control No. 95/001,774, "Aker Biomarine ASA's Corrected Request/Petition for Inter Partes Reexamination of U.S. Pat. No. 8,030,348," filed Oct. 19, 2011, 58 pages.
Inter Partes Reexamination of U.S. Pat. No. 8,030,348, Control No. 95/001,774, "Declaration of Bjorn Ole Haugsgjerd, MSc, in Support of Request for Inter Partes Reexamination of U.S. Pat. No. 8,030,348," dated Oct. 4, 2011, 5 pages.
Inter Partes Reexamination of U.S. Pat. No. 8,030,348, Control No. 95/001,774, First Supplemental Declaration of Bjorn Ole Haugsgjerd, MCs, in Support of Request for Inter Partes Reexamination of U.S. Pat. No. 8,030,348, dated Apr. 16, 2012, 4 pages.
Inter Partes Reexamination of U.S. Pat. No. 8,030,348, Control No. 95/001,774, "Office Action," dated Dec. 19, 2011, 16 pages.
Inter Partes Reexamination of U.S. Pat. No. 8,030,348, Control No. 95/001,774, "Amendment/Response to Office Action," filed Mar. 19, 2012, 68 pages.
Inter Partes Reexamination of U.S. Pat. No. 8,030,348, Control No. 95/001,774, "Action Closing Prosecution," mailed May 14, 2013, 60 pages.
Inter Partes Reexamination of U.S. Pat. No. 8,030,348, Control No. 95/001,774, "Patent Owner Response to Action Closing Prosecution," filed Jul. 15, 2013, 66 pages.
Inter Partes Reexamination of U.S. Pat. No. 8,030,348, Control No. 95/001,774, "Third Party Requester's Comments on Patentee's Response to Action Closing Prosecution," filed Aug. 7, 2013, 22 pages.
Inter Partes Reexamination of U.S. Pat. No. 8,030,348, Control No. 95/001,774, "Declaration of Thomas Gundersen in Support of Request for Inter Partes Reexamination of U.S. Pat. No. 8,030,348," dated Oct. 4, 2011, 67 pages.
Inter Partes Reexamination of U.S. Pat. No. 8,030,348, Control No. 95/001,774, "First Supplemental Declaration of Thomas Gundersen in Support of Request for Inter Partes Reexamination of U.S. Pat. No. 8,030,348," dated Apr. 18, 2012, 42 pages.
Inter Partes Reexamination of U.S. Pat. No. 8,030,348, Control No. 95/001,774, "Declaration of Fotini Sampalis Under 37 C.F.R. 1.132," dated Mar. 16, 2012, 32 pages.
Inter Partes Reexamination of U.S. Pat. No. 8,030,348, Control No. 95/001,774, "Declaration of Richard B. Van Breemen in Support of Inter Partes Reexamination of U.S. Pat. No. 8,030,348," dated Apr. 17, 2012, 114 pages.

Inter Partes Reexamination of U.S. Pat. No. 8,030,348, Control No. 95/001,774, "Declaration of Faustinus Yeboah Under 37 C.F.R. 1.132," dated Mar. 16, 2012, 80 pages.
Inter Partes Reexamination of U.S. Pat. No. 8,030,348, Control No. 95/001,774, "Declaration of Chong M. Lee Under 37 C.F.R. 1.132," dated Mar. 16, 2011, 66 pages.
Inter Partes Reexamination of U.S. Pat. No. 8,030,348, Control No. 95/001,774, "Supplemental Declaration of Dr. Earl White Under 37 C.F.R. 1.132," dated Mar. 16, 2012, 19 pages.
Inter Partes Reexamination of U.S. Pat. No. 8,030,348, Control No. 95/001,774, "Declaration of Jacek Jaczynski Under 37 C.F.R. 1.132," dated Mar. 16, 2012, 221 pages.
Inter Partes Reexamination of U.S. Pat. No. 8,030,348, Control No. 95/001,774, "Declaration of Fereidoon Shahidi Under 37 C.F.R. 1.132," dated Mar. 16, 2012, 160 pages.
Inter Partes Reexamination of U.S. Pat. No. 8,030,348, Control No. 95/001,774, "Patent Owner's Appeal Brief," filed Jul. 21, 2014, 39 pages.
Inter Partes Reexamination of U.S. Pat. No. 8,030,348, Control No. 95/001,774, "Decision on Appeal," dated Dec. 1, 2015, 20 pages.
Inter Partes Reexamination of U.S. Pat. No. 8,057,825, Control No. 95/001,819, "Aker Biomarine's Corrected Request/Petition for Inter Partes Reexamination of U.S. Pat. No. 8,057,825," filed Dec. 16, 2011, 45 pages.
Inter Partes Reexamination of U.S. Pat. No. 8,057,825, Control No. 95/001,819, "Claim Chart regarding Third Party Requestor's Comments to Patentee's Response to Office Action," filed May 16, 2012, 37 pages.
Inter Partes Reexamination of U.S. Pat. No. 8,057,825, Control No. 95/001,819, "Declaration of Nils Hoem in Support of Request for Inter Partes of U.S. Pat. No. 8,057,825," dated Sep. 16, 2011, 31 pages.
Inter Partes Reexamination of U.S. Pat. No. 8,057,825, Control No. 95/001,819, "Declaration of Fereidoon Shahidi Under 37 C.F.R. 1.132," dated Apr. 16, 2012, 185 pages.
Inter Partes Reexamination of U.S. Pat. No. 8,057,825, Control No. 95/001,819, "Declaration of Jacek Jaczynski Under 37 C.F.R. 1.132," dated Apr. 16, 2012, 160 pages.
Inter Partes Reexamination of U.S. Pat. No. 8,057,825, Control No. 95/001,819, "Declaration of Philip Calder in Support of Inter Pales Reexamination of U.S. Pat. No. 8,057,825," dated May 9, 2012, 120 pages.
Inter Partes Reexamination of U.S. Pat. No. 8,057,825, Control No. 95/001,819, "Declaration of Anthony P. Bimbo Under 37 C.F.R. 1.132," dated Apr. 7, 2012, 299 pages.
Inter Partes Reexamination of U.S. Pat. No. 8,057,825, Control No. 95/001,819, "Non-Final Office Action," dated Feb. 17, 2012, 30 pages.
Inter Partes Reexamination of U.S. Pat. No. 8,057,825, Control No. 95/001,819, "Amendment/Response to Office Action," filed Apr. 17, 2012, 55 pages.
Inter Partes Reexamination of U.S. Pat. No. 8,057,825, Control No. 95/001,819, "Third Party Requester Comments to Patentee's Response to Office Action dated Feb. 17, 2012," filed May 16, 2012, 35 pages.
Inter Partes Reexamination of U.S. Pat. No. 8,057,825, Control No. 95/001,819, "Action Closing Prosecution," mailed Jan. 25, 2013, 39 pages.
Inter Partes Reexamination of U.S. Pat. No. 8,057,825, Control No. 95/001,819, "Patent Owner Comments after Action Closing Prosecution," filed Mar. 25, 2013, 69 pages.
Inter Partes Reexamination of U.S. Pat. No. 8,057,825, Control No. 95/001,819, "Third Party Requester Comments in Reply to Patent Owner's Response to Action Closing Prosecution," filed Apr. 26, 2013, 19 pages.
Inter Partes Reexamination of U.S. Pat. No. 8,057,825, Control No. 95/001,819, "Supplemental Patent Owner's Appellant's Brief," filed Jun. 5, 2014, 37 pages.
Inter Partes Reexamination of U.S. Pat. No. 8,057,825, Control No. 95/001,819, "Decision on Appeal," dated Jan. 12, 2015, 29 pages.
Ex Parte Reexamination of U.S. Pat. No. 8,278,351, Control No. 90/012,698, "Petition for Ex Parte Reexamination of U.S. Pat. No. 8,278,351," filed Oct. 2, 2012, 169 pages.

(56) References Cited

OTHER PUBLICATIONS

Ex Parte Reexamination of U.S. Pat. No. 8,278,351, Control No. 90/012,698, "Order Staying Concurrent Ex Parte Reexamination," dated Apr. 2, 2014, 6 pages.
Ex Parte Reexamination of U.S. Pat. No. 8,278,351, Control No. 90/012,698, "Office Action," dated Jan. 2, 2014, 17 pages.
Ex Parte Reexamination of U.S. Pat. No. 8,278,351, Control No. 90/012,698, "Order Granting Request for Ex Parte Reexamination," mailed Dec. 21, 2012, 11 pages.
Ex Parte Partes Reexamination of U.S. Pat. No. 8,278,351, Control No. 90/012,698, "Declaration of Bjorn Ole Haugsgjerd in Support of Request for Ex Parte Reexamination of U.S. Pat. No. 8,278,351," dated Oct. 1, 2012, 4 pages.
Ex Parte Reexamination of U.S. Pat. No. 8,278,351, Control No. 90/012,698, "Declaration of Richard B. van Breemen in Support of Request for Ex Parte Reexamination of U.S. Pat. No. 8,278,351," dated Oct. 1, 2012, 114 pages.
Ex Parte Reexamination of U.S. Pat. No. 8,278,351, Control No. 90/012,698, "Declaration of Ivar Storro in Support of Ex Parte Reexamination of U.S. Pat. No. 8,278,351," dated Sep. 24, 2012, 259 pages.
Inter Partes Reexamination of U.S. Pat. No. 8,278,351, Control No. 90/012,698, "Petition for Inter Partes Review of U.S. Pat. No. 8,278,351," dated Oct. 1, 2013, 64 pages.
Inter Partes Reexamination of U.S. Pat. No. 8,278,351, Control No. 90/012,698, "Declaration of Dr. Ivar Storm in support of Inter Partes Review of U.S. Pat. No. 8,278,351," dated Sep. 26, 2013.
Inter Partes Reexamination of U.S. Pat. No. 8,278,351, Control No. 90/012,698, "Declaration of Dr. Jeff Moore in Support of Inter Partes Review of U.S. Pat. No. 8,278,351," dated Sep. 27, 2013.
Inter Partes Reexamination of U.S. Pat. No. 8,278,351, Control No. 90/012,698, "Declaration of Dr. Richard van Breemen in Support of Inter Partes Review of U.S. Pat. No. 8,278,351," dated Sep. 27, 2013.
Inter Partes Reexamination of U.S. Pat. No. 8,278,351, Control No. 90/012,698, "Declaration of Suzanne Budge in Support of Inter Partes Review of U.S. Pat. No. 8,278,351," dated Sep. 16, 2013, 20 pages.
Inter Partes Reexamination of U.S. Pat. No. 8,278,351, Control No. 90/012,698, "Declaration of Bjorn Ole Haugsgjerd in support of Inter Partes Review of U.S. Pat. No. 8,278,351," dated Sep. 30, 2013.
Inter Partes Reexamination of U.S. Pat. No. 8,278,351, Control No. 90/012,698, "Declaration of Dr. Albert Lee in Support of Inter Partes Review of U.S. Pat. No. 8,278,351," dated Sep. 27, 2013.
Inter Partes Reexamination of U.S. Pat. No. 8,278,351, Control No. 90/012,698, "Declaration of Dr. Thomas Brenna," dated Sep. 29, 2013, 316 pages.
Petition of Aker Biomarine AS for Inter Partes Review of U.S. Pat. No. 8,383,675, IPR 2014-00126, filed Nov. 7, 2013, 64 pages.

NATURAL MARINE SOURCE PHOSPHOLIPIDS COMPRISING POLYUNSATURATED FATTY ACIDS AND THEIR APPLICATIONS

PRIORITY

This application is a continuation of U.S. patent application Ser. No. 14/528,540, filed Oct. 30, 2014, which is a continuation of U.S. patent application Ser. No. 13/750,663, filed Jan. 25, 2013, which is a continuation of U.S. patent application Ser. No. 13/545,830, filed Jul. 10, 2012 (now U.S. Pat. No. 8,383,675, issued Feb. 26, 2013), which is a continuation of U.S. patent application Ser. No. 13/189,714, filed Jul. 25, 2011 (now U.S. Pat. No. 8,278,351, issued Oct. 10, 2012), which is a continuation of Ser. No. 10/485,094, filed Jul. 13, 2004 (now U.S. Pat. No. 8,030,348 issued Oct. 4, 2011), which is a 371 national phase filing of PCT/CA02/001185, which claims the benefit of U.S. Provisional Application Ser. No. 60/307,842, filed Jul. 27, 2001, which is incorporated herein by reference in its entirety.

FIELD OF THE INVENTION

The present invention is directed to nutraceutical, pharmaceutical or cosmetic compositions, particularly to phospholipid compositions derived from natural marine or aquatic sources.

BACKGROUND OF THE INVENTION

WO 92/21335 published on Dec. 10, 1992 and corresponding U.S. Pat. No. 5,434,183 issued on Jul. 18, 1995 describes a phospholipid emulsion derived from marine and/or synthetic origin comprising polyunsaturated fatty acids and having anti-inflammatory and immunosuppressive effects and which promotes-normal brain or retinal development and function. U.S. Pat. No. 5,434,183 does not disclose the presence of flavonoids or nervonic acid (a mono-unsaturated fatty acid) in the composition.

JP 2215351, published on Aug. 28, 1990, discloses a method for extracting and purifying phospholipids from fresh krill. Krill is lyophilized and then extracted with ethanol to produce an extract which is fractionated by absorption column chromatography to produce high purity phosphatidyl choline and phosphatidyl ethanolamine. There is no disclosure of a composition comprising a flavonoid or nervonic acid.

WO 00/23546, published on Apr. 27, 2000, discloses methods for extracting lipid fractions from marine and aquatic animal material by acetone extractions. The resulting non-soluble and particulate fraction is further solvent extracted with ethanol or ethylacetate to achieve further lipid extractions.

Hosokawa et al. (35), published in 2000, discloses the conversion of docosahexanoic acid containing phosphatidylcholines (DHA-PC) from squid skin lecithin to docosahexanoic acid containing phosphadylserines (DHA-PS) via transphosphatidylation with phospholipase D (PLD). According to Table 2 of this reference, the fatty acid composition of the phospholipid includes important portions of eicosapentanoic acid. There is no disclosure concerning any pharmaceutical, nutraceutical, or cosmetic use of a composition comprising a flavonoid.

Henderson et al. (36), published in 1994, discloses lipid compositions of the pineal organ from rainbow trout comprising phospholipids. According to Table 4 of this reference, said phospholipids contain fatty acids corresponding to eicosapentanoic and docosahexanoic acid. Similarly, Bell et al. (37), published in 1991, discloses phospholipid compositions derived from different organs of cod. Moreover, Wiegand et al. (38), published in 1983, discloses polyene derivatives of phosphatidylcholine as phospholipid molecular species of frog receptor membranes. However, there is no disclosure in any of these references concerning any pharmaceutical, nutraceutical, or cosmetic use of a composition comprising a flavonoid.

WO 97/39759, published on Oct. 30, 1997, discloses ω-3 fatty acids and ω-3 phosphatidylcholine in the treatment of bipolar disorder. The preferred ω-3 phosphatidylcholine derivatives comprise eicosapentanoic and/or docosahexanoic acid. However, there is no disclosure concerning any pharmaceutical, nutraceutical, or cosmetic use of phospholipids beyond the treatment of bipolar disorder or the use of a composition comprising a flavonoid.

EP 0609078 A1, published on Mar. 8, 1994, discloses a phospholipid comprising two different unsaturated fatty acids, wherein a preferred phospholipid contains both eicosapentanoic and docosahexanoic acid. Furthermore, the phospholipid can be used in the preparation of foods, skin care preparations, or pharmaceutical agent. However, there is no disclosure concerning any pharmaceutical, nutraceutical, or cosmetic use of a composition comprising a flavonoid.

SUMMARY OF THE INVENTION

In one aspect, the invention provides novel phospholipids, wherein the two fatty acids chains of the phospholipid are occupied by eicosapentanoic acid (EPA) and docosahexanoic acid (DHA) simultaneously, within the same molecule, i.e.: a phospholipid of the general formula (I):

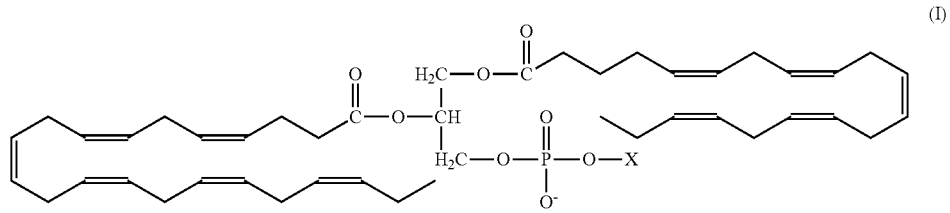

wherein X represents a moiety normally found in a phospholipid.

According to a further aspect of the present invention there is provided a composition, comprising:
(a) a phospholipid of the general formula (I),

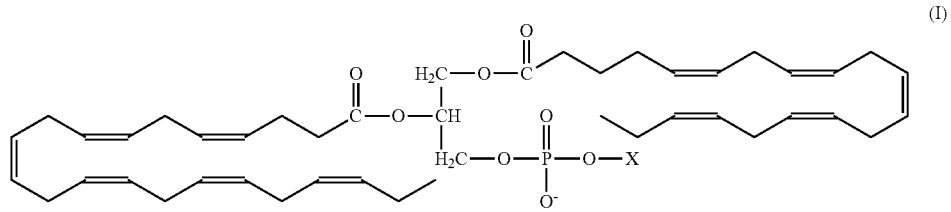

wherein X is —CH$_2$CH$_2$NH$_3$, —CH$_2$CH$_2$N(CH$_3$)$_3$ or

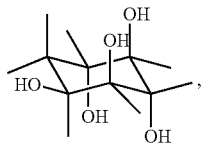

and
(b) a flavonoid of the general formula (II),

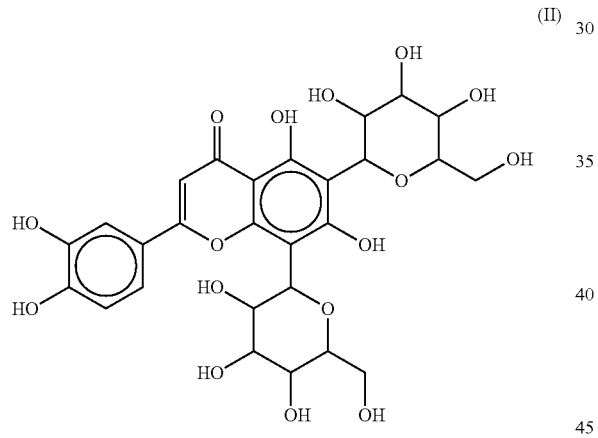

In a further aspect, the invention provides a novel flavonoid compound (II):

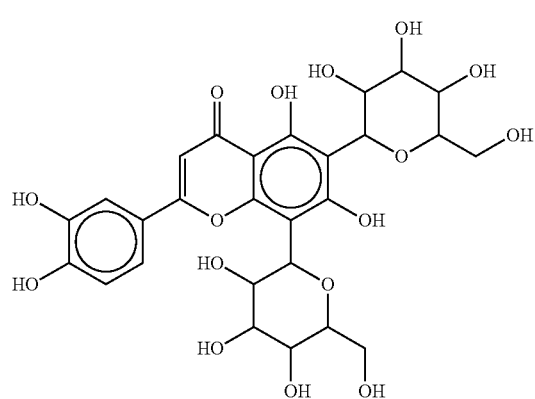

There is also provided a composition comprising the above noted phospholipid and flavonoid derived from a marine or aquatic biomass. The composition and the components are useful in the prevention or treatment of a variety of disease states and for the aesthetic enhancement of an animal, including human, body. Commercial packages containing the composition are also within the invention.

The novel phospholipids and the novel flavonoid compound are derived from an extract from a marine or aquatic biomass.

There is also provided a phospholipid extract comprising the above noted phospholipids and flavonoid compound derived from a marine or aquatic biomass. The extract and the components are useful in the prevention or treatment of a variety of disease states and for the aesthetic enhancement of an animal, including human, body. Pharmaceutical, nutraceutical and cosmetic compositions containing the extract and uses thereof are also within the invention, as are commercial packages contain the compositions of the invention.

DETAILED DESCRIPTION OF THE INVENTION

1. Phospholipids

Phospholipids are complex lipids containing phosphorus. The phosphatides, known as phospholipids, are usually divided into groups on the basis of compounds from which they are derived. In addition to two chains of fatty acids they contain phosphoric acid, glycerol and nitrogenous bases such as choline. Important phospholipids are phosphatidylcholine (PC), phosphatidylethanolamine (PE) and phosphatidylinositol (PI). Their nature as amphophilic molecules provides them with unique physicochemical properties. Their function as the principle components of cell membranes makes phospholipids essential for all vital cell processes. They are wide spread as secretory and structural components of the body and can mimic or enhance natural physiological process.

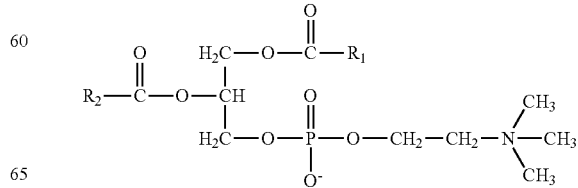

Phosphatidylcholine—common Structure
$R_1$ and $R_2$ are fatty acid residues,
different for each molecular species

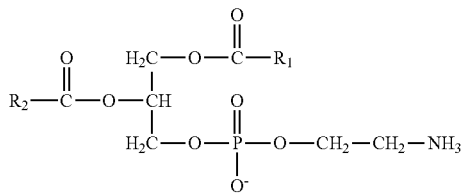

Phosphatidylethanolamine—common Structure
$R_1$ and $R_2$ are fatty acid residues,
different for each molecular species

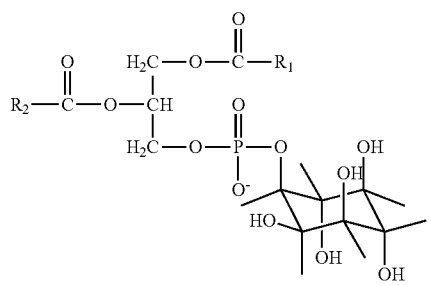

Phosphatidylinositol—common Structure
$R_1$ and $R_2$ are fatty acid residues,
different for each molecular species Phospholipid production may be either synthetic or through extraction from natural tissues. The chief source of commercial natural phospholipids are soybean, egg yolk and cows (brain and liver). Since an individual phospholipid may contain a variety of fatty acid residues, it may be described as pure only with this limitation in mind. Naturally occurring essential polyunsaturated fatty acids can contribute to the activation of cellular metabolism. The main fatty acid found in phospholipid products is linoleic acid (C18: 2n6), present in soybean at more than 65%. The longest chain polyunsaturated fatty acids found in commercially available phospholipids either as preparations or individually are 20:4 among the eicosanoids, known as arachidonic acid, and 22:6 known as docosahexanoic acid.

Arachidonic acid is a fatty acid that is found as part of phospholipid membranes, generally as part of phosphatidylcholine and phosphatidylinositol. Adverse cellular stimuli will activate enzymes (phospholipase) that cleave arachidonic acid from the phospholipid backbone in the cell membrane. Arachidonic acid, which serves as the precursor for prostaglandins and prostacyclin (PGs, $PGI_2$) and thromboxane (TXs), can then be metabolized by one of two major pathways: the cyclooxygenase (COX) pathway or the lipoxygenase pathway. The COX pathway products, $PGG_2$ and $PGH_2$, can then be acted upon by thromboxane synthase (in platelets) or prostacyclin synthase (in endothelium) to form TXs or $PGI_2$, respectively. Arachidonic acid can also be acted upon by 5-lipoxygenase, primarily in leukocytes, to form leukotrienes (LTs). One or more of these metabolites can mediate all the signs and symptoms associated with arachidonic acid, i.e. inflammatory disease and pain.

Platelets, leukocytes, smooth muscle, and endothelium can produce vasoactive substances, products of arachidonic acid metabolism such as prostaglandins (PGs), prostacyclin ($PGI_2$), leukotrienes (LTs), and thromboxanes (TXs). These substances can either act as vasodilators or as vasoconstrictors. $PGI_2$ is essential in vascular function since it inhibits platelet adhesion to the vascular endothelium and has significant vasodilatation qualities. Damaged endothelial cells cannot produce $PGI_2$, making the vessel more susceptible to thrombosis and vasospasm. Thromboxanes and leukotrienes serve a vascular function during inflammation, generally producing vasoconstriction. Prostaglandins have a vascular role during inflammation, and also play a more subtle role in normal flow regulation, most notably as modulators of other control mechanisms. Prostaglandins have both vasoconstrictor and vasodilator activities. Leukotrienes and prostaglandins can also increase the endothelial membrane permeability thus promoting edema during inflammation. Arachidonic acid is naturally present in most phospholipid mixtures or emulsions available today.

Nervonic acid (C24:1) is also called selacholeic acid or tertracosenic acid. Nervonic acid is the predominant nutrient of white matter in glucoside, which is quantitatively contained in nerve tissue and white matter. The absence of nervonic acid may result in cerebral lesion, fatigue, hypodynamia, amentia, and senile dementia. Nervonic acid, tertracosenic acid in another name, is monounsaturated, non-oxidable/decomposed and absorptive. It is called a rare tonic as it is rare existent in nature. It may be obtained in small quantities by extracting from cerebral chrondriosome. Therefore, the substantance is far below the demand of human body. In foreign countries, nervonic acid mainly comes from shark brain and oil.

1.1 Phosphatidylinositol Clinical Applications

Recent advances in nutritional and biochemical research have documented inositol as an important dietary and cellular constituent. Functions of phosphatidylinositol in biological membranes include the regulation of cellular responses to external stimuli and/or nerve transmission as well as the mediation of enzyme activity through interactions with various specific proteins (1).

Inositol has been identified as an important dietary and cellular constituent. Biochemical functions:
a. Regulation of cellular responses to external stimuli
b. mediation of enzyme activity.

Phosphoinositide composition of the central nervous system cell membranes are fatty-acid enriched and consist primarily of phosphatidylinositol (PI), phosphatidylinositol-4-phosphate (PIP), and phosphatidylinositol-4,5-biphosphate (PIP2). Once the membrane is stimulated, phospholipase C is activated and consequently inositol triphosphate along with diacylglycerol is produced. PI is used as a precursor for phosphatidylinositol-3-phosphate and 3,4,5-triphosphate (2).

Active transport carriers, calcium pumps in the cell membrane itself, and in the endoplasmic reticulum, keep cytoplasmic calcium concentration very low. Usually the calcium concentration inside the cytoplasm is 5,000-10,000 times less than the concentration in the extracellular fluid. This endoplasmic store of calcium can be accessed upon stimulation by inositol. Inositol triphosphate is released from the cell membrane and travels through the cytoplasm until it reaches the endoplasmic reticulum. This inositol then releases the sequestered calcium, which can go on to mediate the release of neurotransmitters in response to depolarization (3).

In addition to releasing endoplasmic reticulum calcium, inositol functions as the major central nervous system non-nitrogenous osmoregulator. Modulation of this inositol pool is regulated in response to states of high or low osmolalities. The inositol pool is supplied via a sodium/inositol transporter, a sodium dependent active transport system, and a passive low affinity transporter (4, 5).

Numerous non-inositol receptors have been identified in the central nervous system that can potentially interact with the inositol signaling system. Most of these receptors are linked to the G proteins and produce inositol-1,4,5-triphosphate as second messengers. These receptors can be found in nearly every human organ system. The potential interactions between these receptors and their agonists are responsible for regulation of the body on a day-to-day basis. In view of the complexity of these systems and their actions, a perfect balance is required for regulation of the signaling systems.

Theoretically, an imbalance of inositol concentration could potentially affect the development and function of one or all of these receptors. Cholinergic receptors are located in the liver, heart, stomach, and lungs. Serotonin and glutamine receptors are found mostly in the central nervous system (CNS) tissues. Adrenergic receptors are present in various tissues including CNS, vascular tissues, and heart. Histaminergic receptors are predominantly found in the lungs and stomach.

Clinical Applications

A change in CNS availability of inositol may produce altered brain signaling and eventually lead to the development of neurological disorders.

a. Depression:

The pathophysiology of depression is believed to be linked to a deficiency of neurotransmitters at post-synaptic receptor sites. According to the catecholamine theory, the deficiency is in the amount of norepinephrine; in the indolamine theory the deficiency is in the amount of serotonin. Receptors linked to the inositol signalling system include serotonin (5HT2a and 5HT2b) and norepinephrine (alpha 1a, 1b, and 1d).

In 1978, Barkai et al demonstrated depressed patients had significantly decreased cerebospinal fluid (CSF) levels of inositol as compared to healthy patients (6). In 1993 this theory was expanded to conclude that administration of high-dose inositol could increase CSF levels by as much as 70 percent (7). This led to the study of inositol for treatment of depression (8, 9). In 1995 Levine et al completed a double-blind study for treatment of depression using inositol at a dose of 12 grams daily compared to placebo. Patients receiving inositol showed significant improvement in depression as ranked by the Hamilton Depression Rating Scale (33.4+/−6 versus 0.6+/−10). Another important observation was the absence of manic episodes in the bipolar patients treated with inositol. This lack of manic episodes may suggest that when the signalling system is not overactive, addition of inositol will not increase the signalling system's activity (10, 11). It can be concluded that inositol is effective in managing the clinical manifestations of depression.

b. Panic Disorder:

Benjamin et al expanded the clinical use of inositol by evaluating its effectiveness in panic disorder (12). This was an eight week double-blind, crossover study whereby patients were treated with inositol daily for four weeks and then crossed over to the other study arm. Improvement was assessed using patient diaries, the Marks-Matthews Phobia Scale, the Hamilton Anxiety Rating Scale, and the Hamilton Depression Scale. The frequency and severity of panic attacks and the severity of agoraphobia declined significantly more after inositol than after placebo (a decrease from 10 attacks per week to 3 per week in the treated group compared to a decrease from 10 to 6 in the placebo group). The authors conclude inositol's efficacy and safety, and the fact that inositol is a natural component of the human diet, make it a potentially attractive therapeutic agent for panic disorder.

c. Obsessive Compulsive Disorder (OCD):

Since the phosphatidylinositol cycle, as a second messenger is known to affect several neurotransmitters, including serotonin receptors, inositol was studied for treatment in OCD in a double-blind, placebo controlled, crossover trial. Thirteen patients were treated for six weeks. There was a significant improvement at week six during the inositol period when compared to placebo period. There were no side-effects reported during the study period (1).

d. Alzheimer's Disease (AD):

Although the role of aluminum in AD is still speculative at best, the presence of aluminosilicates at the core of senile plaques in diseased neurons is a consistent feature found in the CNS of AD patients during autopsy. It is known that aluminum inhibits the incorporation of inositol into phospholipids and the hydrolysis of the phosphoinositides by binding to one of two specific phosphate groups. This binding of phosphate and aluminum affects the calcium releasing effects of the cell. The resulting profound disturbance of the phosphatidylinositol second messenger system may account for neuronal malfunction and eventual cell death (13).

Since the potential role of aluminum as a causative agent for cell death may be affected by the deregulation of calcium concentration, possibly due to inositol depletion, supplementation with inositol may produce positive CNS effects. Recent data suggests the loss of PI second messenger system target sites and IP3 receptors may add to cognitive impairment and the failure of conventional therapies in AD. Therefore, supplementation of inositol to replenish the diminished PI system may be beneficial in the treatment of AD (13-20).

In 1996 Barak et al completed a double-blind, controlled, crossover study of six grams inositol daily compared to placebo for 30 days in 11 Alzheimer's patients. Patients in the study were diagnosed with dementia of the AD type as classified by DSM-IIIR and aged 65 years or older. The Cambridge Mental Disorder of the Elderly Examination (CAMDEX) was used as the basic assessment parameter and was administered upon admission into the study. Included in CAMDEX is part A: patient's present physical and mental state, part B: Cognitive Subscale of CAMDEX (CAMCOG), part C: interviewers observations, and part D: physical examination. CAMCOG was repeated at two, four, six, and eight weeks. Participants scored 80 or less on the CAMCOG examination and their symptoms of depression were not severe (21).

Patients were excluded from the study if they had a history of psychiatric, alcohol, and/or drug addiction disorders, or abnormalities in baseline laboratory values (blood count, electrolytes, liver or kidney functions, VDRL, or CT scan) not consistent with AD. Patients with additional neurologic, metabolic, endocrinologic disorders, or presence of internal disease that grossly impaired brain functioning were also excluded.

Subjects were given either three grams inositol or placebo in the morning and again in the evening. After four weeks patients were crossed over into the other arm (inositol or placebo) for an additional four weeks. Only benzodiazepines were allowed during the study period (15 mg of oxazepam or equivalent), provided the patient was receiving it on study entry.

Analysis of the improvement scores of all patients who completed the study showed inositol increased the total CAMCOG score from a baseline of 31.36+/−20.90 to 40.09+/−24.54, while the placebo group increased from baseline of 35.9+/−25.96 to 39.27+/−25. The authors concluded only two of the eight subscales (language and orientation) showed significant improvement with inositol.

Inositol's proposed mechanism of action in the CNS does not include direct manipulation with either pre- or post-receptors. However, it may indirectly affect the relationship between receptor and agonist. By mediating the physio-chemical characteristics of the M1 pre-synaptic receptor (solubility, osmolality, etc.), inositol may alter the binding site and influence the signaling that occurs as a result.

1.2 Aging

Phosphatidylcholine rich in polyunsaturated fatty acids is indispensable for cellular differentiation, proliferation and regeneration. The physiologic functions of these phospholipids are related to the morphology of the biological membranes, the incorporation of these molecules into membranes and thus the maintenance of intact cell membranes.

The current study was designed to investigate the effects of Polyunsaturated phosphatidylcholine on age-related hearing loss by evaluating its ability to preserve mitochondrial function, protect mitochondrial DNA from oxidative damage and preserve auditory sensitivity (22).

Harlan-Fischer 344 rats, 18-20 months of age, were used as the experimental subjects.

The subjects were caged individually and maintained at 21 to 22° C. in a 12:12 light-dark cycle b.

A dose of 300 mg/kg/day of Polyunsaturated phosphatidylcholine was supplemented to each subject, by adding it to the oral diet.

The animals were divided randomly into two groups (n=7 for each group). Group-1 served as the control, and group-2 as the experimental group.

At the onset of the study, Auditory Brainstem Responses were obtained to measure baseline hearing thresholds in all subjects.

Age-associated changes in hearing sensitivities were then recorded at two-month intervals for six months.

In order to assess age-related changes in mitochondrial function, mitochondrial membrane potentials were studied using flow cytometry. For this purpose, peripheral blood was obtained from each subject at the beginning and at the end of the protocol.

At the conclusion, the subjects were euthanized (according to NIH protocol), and tissue samples were obtained from brain and cochlea (stria vascularis and auditory nerve) to study mitochondrial DNA deletion associated with aging. This was achieved by amplifying the specific common aging mitochondrial deletion by Polymerase Chain Reaction. DNA quantification was performed. The data obtained for each protocol was compared between the two groups and analyzed using ANOVA.

The effects of Polyunsaturated phosphatidylcholine on age-related hearing loss demonstrate a gradual age-associated decline in hearing sensitivities at all the frequencies tested (3, 6, 9, 12 and 18 kHz).

There was a statistically significant preservation of hearing noted in the treated subjects at all frequencies, which was observed at four and six months of treatment.

Overall, there was a continued decline in hearing in the control subjects and a statistically significant protective effect of Polyunsaturated phosphatidylcholine on the experimental subjects ($p<0.005$).

Mitochondrial membrane potentials were recorded by flow cytometry as a measure of the uptake of Rhodamine 123 by mitochondria.

The mean fluorescence intensity (MFI) in group-1 subjects measured 3190 and 2100 at the beginning and end of the study, respectively.

This, approximately, 30% decline in membrane potential with time was statistically significant ($p=0.003$).

Conversely, the MFI in the experimental group remained essentially unchanged at 2990 from 3165 at the beginning of the study.

This difference between the control and treated groups was statistically significant ($p<0.05$), demonstrating the protective effect of polyunsaturated phosphatidylcholine supplementation on mitochondrial membrane potential.

Phospholipids are integral structural components of all biological membranes with polyunsaturated phosphatidylcholine and phosphatidylethanolamine being the predominant types, quantitatively. They constitute the phospholipid bilayer structure of cellular membranes, which is responsible for membrane stability and cellular function. Polyunsaturated phosphatidylcholine maintains and promotes the activity of several membrane bound proteins and enzymes, including Na-K ATPase, adenylate cyclase and glutathione reductase. They are also known to be precursors of cyto-protective agents such as eicosanoids, prostaglandins and antioxidants.

The results of these studies suggest that polyunsaturated phosphatidylcholine and phosphatidylethanolamine may protect mitochondrial function by preserving the age-related decline in mitochondrial membrane potentials and hence their activity. The observation that there was less mitochondrial DNA damage in the treated group may explain the effect of preservation of hearing loss associated with aging, by the ability of polyunsaturated phosphatidylcholine and phosphatidylethanolamine to specifically up-regulate cochlear mitochondrial function. There are many studies demonstrating the effects of mitochondrial metabolites on cognition and aging (22-33). Additionally, recent work has shown that acetyl-L-carnitine and -lipoic acid delay the progression of age-related hearing loss by protecting cochlear mitochondrial DNA from oxidative damage (34). These results support the membrane hypothesis of aging and provide further evidence to support this theory as a possible explanation for age-related hearing loss. Thus, PPC may be one of many rational approaches to consider for the purpose of membrane preservation, enhanced mitochondrial function, reduction of age-associated mitochondrial DNA damage and slowing of some of the aging processes.

1.3 Effect of Phosphoglycolipid Extract (NT Factor) on Normal and Cancerous Cells Reduced levels of phospholipids in normal cells can limit metabolic activity and limit available energy. Phospholipids, as part of the membrane structure:

(a) maintain membrane integrity.
(b) regulate enzyme activities and membrane transport processes through changes in membrane fluidity (Spector 1981, 1985).
(c) Signal transduction utilizes phospatidylcholine and phosphatidylinositol for the production of diacyl-glycerol (DAG) by phospholipase C (Berridge 1989) and for the production of inositol triphosphate (IP3) (Ranan 1990, Michell 1988, Margolis 1990).
(d) One of the choline phospholipids (1-alkyl-2 acetyl-SN-glycerol-3-phosphocholine) is the substrate for the synthesis of platelet activating factor (Synder 1989).

(e) The arachidonic acid found as part of the structure of choline or inositol phospholipid is utilized for the production of prostaglandin and leukotriene (Nordoy 1990).
(f) The choline of phosphatidylcholine may be used in neural tissue for the synthesis of acetylcholine (Blusztain 1987).
(g) Phosphoglycolipid improves cell maintenance and metabolic activity of normal cells.
(h) Phosphatidylcholine derivatives disrupt cancer cells at concentrations that do not affect normal cells.
(i) Phosphatidylcholine is selectively cytotoxic to cancer cells in vitro (Hoffman 1986, Harmann 1986, Berger 1984).
  (i) Such compounds inhibit HL60 leukemic cells at a dosage that has no effect on normal human marrow cells, the tissue from which the leukemic cells are derived.
  (ii) Normal cells were able to tolerate 4 times higher dosage than the leukemic cells during 24 hours incubation with the phospholipid preparation (Berdel 1986).
  (iii) There was up to a 5-fold difference in sensitivity between the normal and tumor cells with breast, ovarian, and lung cancer cells, as well as with mesothelioma cells (Namba 1993).

1.4 Imaging

Polyunsaturated phospholipids are known to be important with regard to the biological functions of essential fatty acids, for example, involving neural tissues such as the brain and retina. The NMR spectra of polyunsaturated bilayers are dramatically different from those of less unsaturated phospholipid bilayers. MD simulations can aid in interpreting the complex NMR spectra of polyunsaturated bilayers, in conjunction with electron density profiles determined from small-angle X-ray diffraction studies. This work clearly demonstrates preferred helical and angle-iron conformations of the polyunsaturated chains in liquid-crystalline bilayers, which favor chain extension while maintaining bilayer flexibility. The presence of relatively long, extended fatty acyl chains may be important for solvating the hydrophobic surfaces of integral membrane proteins, such as rhodopsin. In addition, the polyallylic DHA chains have a tendency to adopt back-bended (hairpin-like) structures, which increase the interfacial area per lipid. Finally, the material properties have been analyzed in terms of the response of the bilayer to mechanical stress. Simulated bilayers of phospholipids containing docosahexaenoic acid were less sensitive to the applied surface tension than were saturated phospholipids, possibly implying a decrease in membrane elasticity (area elastic modulus, bending rigidity). The above features distinguish DHA-containing lipids from saturated or nonunsaturated lipids and may be important for their biological modes of action.

1.5 In Summary

The functions of the phospholipids are multiple and different for each phospholipid:
(a) Sphingosine and carbohydrate containing lipids are mainly concentrated in nervous tissues.
(b) The hydrophilic and hydrophobic parts of the phospholipid molecule allow them to function as emulsifying agents in order to maintain the proper colloidal state of protoplasm.
(c) Phospholipids aid the transport of triglycerides through the liver, especially during mobilization from adipose tissue.
(d) Phospholipids and their metabolites play an important role in intracellular signalling, for example via phosphatidylinositol specific phospholipase C, phospholipase D or phosphatidylinositol-kinases.
(e) Through their concentration in cell membranes they may somehow be involved in the transport of hydrophobic constituents into and out of cells.
(f) Phospholipids affect brain function in two substantial ways: (Cohen B. M., Babb S. M., Yurgelun-Todd D., et al. *Brain choline uptake and cognitive function in middle age. Biol. Psych.* 1997; 41:90S.)
  (i) The membranes of brain cells depend on phospholipids as part of their structure. Phosphatidylserine (PS) is concentrated in the cell membranes of the brain.
  (ii) Phospholipids are required for the production of neurotransmitters.
  (iii) Choline is a component of the neurotransmitter acetylcholine. Without adequate levels of acetylcholine, the brain can't store or retrieve information efficiently.
  (iv) Lower choline levels in the brain are an underlying factor for age-related cognitive disorders.
  (v) Patients submitted to increased choline uptake show significant improvement in their ability to recall information and perform on memory retention tests, suggesting a causal relationship between poor choline status and cognition.
(g) Phosphatidylserine (PS) in Dementia-Related Diseases:
  (i) Dementia is the deterioration of mental function, particularly affecting memory, concentration, and judgment.
  (ii) A frequent cause of dementia is Alzheimer's disease.
  (iii) The first double-blind trial of PS for Alzheimer's disease was published about a decade ago. (Delwaide P. J., et al. *Double-blind randomized controlled study of phosphatidylserine in demented subjects. Acta Neur. Scand.* 1986; 73:136-140.) In this study, 35 Alzheimer's patients were either given a placebo or 300 mg. per day of PS for six weeks. The PS group showed significant improvement after this short-term supplementation period.
  (iv) More recently, a large double-blind study of 494 elderly patients with symptoms of cognitive decline compared a placebo to 300 mg. per day of PS for six months. (Cenacchi T, Bertoldin T, Farina C., et al. *Cognitive decline in the elderly: A double-blind, placebo-controlled multicenter study on efficacy of phosphatidylserine administration. Aging Clin. Exp. Res.* 1993; 5:123-133.) Memory and learning of the PS-treated group was significantly improved over the placebo group, as well as certain emotional and behavior components of Alzheimer's disease.
  (v) Supplements of PS have also shown impressive results in older populations with memory impairment unrelated to Alzheimer's disease. (Crook T. H., et al. *Effects of phosphatidylserine in age-associated memory impairment. Neurology* 1991; 41:644-649.) Three months of taking 300 mg. of PS daily, in one study, reversed the decline of memory function in a group of 149 patients. The memory function of these men and women initially averaged that of a typical 64 years old. After taking PS supplements, the average memory function was 52 years old—a mental gain of 12 years.

(h) Restoring and Preserving Liver Function:
  (i) While the phospholipid PS dominates in the mental function arena, the phospholipid phosphatidylcholine (PC) is the major player for liver health.
  (ii) PC protects the liver against damage from alcoholism, pharmaceuticals, pollutant substances, viruses, and other toxic influences, most of which operate by damaging cell membranes.
  (iii) Many of the studies using PC supplements to aid recovery of the liver are based on 800 mg. per day (taken with meals). (Kidd P. M. *Phosphatidylcholine: A superior protectant against liver damage. Alt. Med. Rev.* 1996; 1:258-274.) Although PC is a source of choline, studies reviewed by Dr. Kidd suggest that PC is superior to choline; in fact choline in its pure form may be detrimental to the liver's recovery from toxic overload (such as in alcoholism). As a lipotropic, choline transports fats within the body, while inadequate choline intake might result in an unhealthy accumulation of fat in the liver. (Newberne P. M., Nauss K. M., and de Camargo J. L. *Lipotropes, iunmunocompetence, and cancer. Cancer Res.* 1983; 43:2426S-2434S.)

2. Flavonoids

Flavonoids are polyphenolic compounds ubiqitous in nature. They are categorized into isoflavones, anthocyanidins, flavans, flavonols, flavones, citrus flavonoids, hesperidin, chalcones, catechins, rutin, and flavanones. Essential flavonoids, such as quercetin in onions and genistein in soy are actually considered subcategories rather than independent categories. Over 4,000 flavonoids have been identified in fruits, vegetables and beverages (tea, coffee, beer, wine and fruit drinks). Even though they have a similar molecular structure between them, their functions are different from each other. Flavonoids have been shown to have antibacterial, anti-inflammatory, antiallergic, antimutagenic, antiviral, antineoplastic, anti-thrombotic, and vasodilatory activity. Quercetin has been proven to block the "sorbitol pathway" which is directly associated with diabetes as well as to prevent LDL-cholesterol oxidative damage, which is essential for the maintenance of a healthy cardiovascular system.

Flavonoids are found in a wide range of fruits and vegetables. For example, Quercetin (a flavonol in vegetables, fruit and onions), Xanthohumol (a prenylated chalcone in beer), Isoxanthohumol (a prenylated flavanone in beer), Genistein (an isoflavone in soy), Chalconaringenin (a non-prenylated chalcone in citrus fruits) and Naringenin (a non-prenylated flavanone in citrus fruits).

In plants flavonoids have very well defined functions. First, the accumulation of pigment in flower petals, seeds and leafs. Flowers, as pollinators, must attract pollen carriers. Second, they protect plants from UV damage, by absorbing UV at the epidermal layer. Third, they protect the plants against insects and pathogens.

The flavonoid biosynthetic pathway is one of the best understood plant secondary metabolism pathways (1992, Gerats). The key enzymes are phenylalanine-ammonia lyase and chalcone synthase. Phenylalanine-ammonia lyase converts phenylalanine into cinnamic acid as it controls the total flow of carbons into phenolics which is shown to be the limiting step in this pathway (1974, Creasy). Another key enzyme of the flavonoid pathway is the chalcone synthase. It condenses three molecules of malonyl-CoA with one molecule p-courmaroyl-CoA to form a $C_{15}$ intermediate, naringenin chalcone, with a R stereochemistry at the $2^{nd}$ carbon. Chalcone isomerase, transforms the intermediate into the first flavonoid of the pathway, 2S-flavonone (naringenin). This reaction is part of all major flavonoid biosynthesis pathways. Chalcone synthase and chalcone isomerase form a complex ensuring the right stereochemistry (1996, Lyster).

The structural components of flavonoids include two benzene rings on either side of a 3-carbon ring. Different combinations of hydroxyl groups, sugars, oxygens, and methyl groups attached to these structures create the various categories of flavonoids mentioned above. The capacity of flavonoids to act as an antioxidant depends upon their biochemical structure, and more specifically, the position of the hydroxyl groups. Epicatechin gallate, epigallocatechin gallate, luteolin and quercetin exhibit the highest antioxidant activity, followed by epigallocatechin, gallic acid, epicatechin, catechin, rutin, and dihydroquercetin. It is worth noting at this point that the only difference between quercetin or luteolin (the most potent) and dihydroquercetin (the least potent) is the double bond between the second ($2^{nd}$) and third ($3^{rd}$) carbons on the center (C) ring. The presence of this double bond significantly increases the antioxidant activity of the flavonoid. Antioxidant activity can be increased with the addition of another hydroxyl group on the B or C ring.

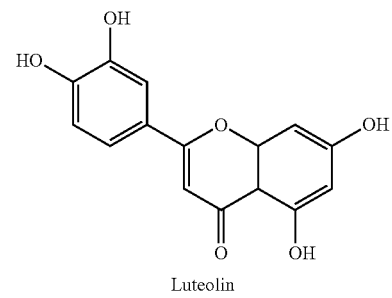
Luteolin

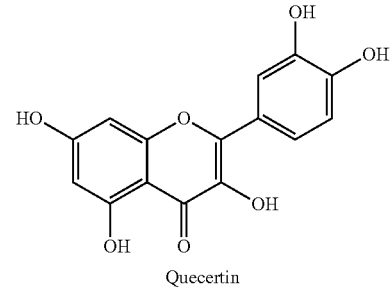
Quecertin

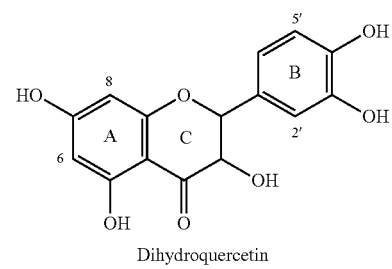
Dihydroquercetin

The potent antioxidant activity of flavonoids seems to be the most important function of flavonoids, responsible for many of the above mentioned health benefits.

The flavonoids most recognised by scientists until today are:
Quercetin and Quercetin Chalcone Quercetin chalcone, is quercetin with an opened C ring and the oxygen found in the C-ring of quercetin converted into a hydroxyl group. Quercetin is mainly found in tea and even more in green tea.

Oligomeric Proanthocyanidins

Oligomeric proanthocyanindins are oligomeric flavonoids, usually dimers and trimers, based on the flavan-3-ol, or catechin, molecule, sometimes attached to gallic acid. They are found in the bark of pine trees, in grape seeds and skins, in peanut skins, cranberries, tea, and other sources.

Ginkgo Biloba Extract

Ginkgo biloba extracts contain 24% ginkgo flavone glycosides and 6% terpenes. They are extracted from the eldest living tree species, Gingo Biloba. Scientific research suggests that the beneficial constituents of ginkgo biloba extracts are quercetin and myricetin.

Luteolin

Luteolin is a flavonoid found in the same foods as apigenin (vegetables and fruits). Scientific research has shown that luteolin and quercetin can inhibit platelet activating factor and suppress the inflammatory response induced by allergens.

Flavonoids have been studied for the last 60 years. Their antioxidant activity is accepted as a scientific fact. Epidemiological, clinical, and laboratory research on flavonoids demonstrates the use of flavonoids in the prevention and/or treatment of cardiovascular disease, cancer, inflammatory conditions, asthma, peridontal disease, liver disease, cataracts and macular degeneration. Until today there has never been a flavonoid extracted from anything other than a plant, vegetable, fruit or algae.

3. Preparation of Extracts

The phospholipid extract of the present invention may be extracted from a variety of marine or aquatic biomass sources. Preferred sources of the phospholipid composition are crustaceans, in particular, zooplankton. A particularly preferred zooplankton is Krill. Krill can be found in any marine environment around the world. For example, the Antarctic Ocean (where the krill is Euphasia superba), the Pacific Ocean (where the krill is Euphasia pacifica), the Atlantic Ocean and the Indian Ocean all contain krill habitats. In particular, the coastal regions of Mauritius Island and/or Reunion Island off Madagascar, the Canadian West Coast, the Japanese Coast, the Gulf of St. Lawrence and the Bay of Fundy are krill habitats.

The phospholipid extract of the present invention is preferably a product of initial processing of the biomass. As such, the phospholipids are extracted from the biomass grease as opposed to the oil, the oil being a product of subsequent processing steps of a biomass. Since the phospholipid extract is derived from the biomass grease, the viscosity of the phospholipid extract tends to be higher than extracts from biomass oils. The extract has a very high natural stability with a peroxide value of zero or approaching zero and a good Oil Stability Index of less than about 0.2 Meq/kg after 20 or more hours. Table 1 below details the stability of the extract.

TABLE 1

Stability indexes of the extract after 50 hours at 97.8° C.

| | |
|---|---|
| Peroxide value (mEq/kg) | <0.1 |
| Oil Stability Index (after 50 hours) at | <0.1 |

TABLE 1-continued

Stability indexes of the extract after 50 hours at 97.8° C.

| 97.8° C. (mEq/kg) | |
|---|---|
| Saponification Index | 70-180 |
| Iodine Index (%) | 60-130 |

Phospholipids are generally present in the extract in an amount of at least 40% w/w, preferably at least 45% w/w. More preferably, the amount of phospholipid is from about 45-60% w/w. A variety of types of phospholipids may be present in the extract. These include phosphatidylethanolamine, phosphatidylinositol, phosphatidylserine, phosphatidylcholine and sphingomyelin.

The phospholipid extract preferably further comprises a number of other components. The extract may also comprise fatty acids, antioxidants and/or metals.

Fatty acids found in the phospholipid extract may be saturated, monounsaturated or polyunsaturated fatty acids. Polyunsaturated fatty acids are particularly preferred, the omega-3 and omega-6 fatty acids being most preferred. In particular, docosahexaenoic acid (DHA), eicosapentaenoic acid (EPA), myristic acid, myristoleic acid, lignoceric acid, linolenic acid, alpha linolenic acid, nervonic acid, linoleic acid, oleic acid, stearic acid, palmitic acid and palmitoleic acid are present in significant quantities. Arachidonic acid content of the extract is generally very low to non-existent despite the presence of phosphatidyl inositol and phosphatidyl serine. Other lipid components that may be present in the extract include monoglycerides, triglycerides and/or cholesterol.

Table 2 below details the fatty acid compositions of the phospholipids of the extract.

TABLE 2

The fatty acid composition of the extract of the phospholipids

| Fatty Acids | Total PL FA % | PC FA % | PE FA % |
|---|---|---|---|
| C14:0 MYRISTIC | 2.04 | 1.70 | 0.7 |
| C14:1 MYRISTOLEIC | 1.22 | | |
| C15:0 PENTADECANOIC | 0.2 | 0.30 | 0.3 |
| C16:0 PALMITIC | 24.08 | 26.50 | 23.9 |
| C16:1 PALMITOLEIC | 2.24 | 2.30 | 0.7 |
| C18:0 STEARIC | 1.02 | 1.30 | 2.9 |
| C18:1 OLEIC | 9.18 | 11.90 | 24.1 |
| C18:2n6 LINOLEIC | 1.63 | 2.30 | 0.8 |
| C18:3n6 GLA | 1.02 | 0.30 | |
| C18:3n3 ALA | 1.02 | 1.30 | |
| C18:4n3 OTA | 1.84 | 2.00 | 0.3 |
| C20:0 ARACHIDIC | | | |
| C20:1 cis-11-EICOSENOIC | 0.41 | 0.60 | 0.7 |
| C20:2n6 EICOSADIENOIC | | | |
| C20:3n6 METHYL ETA | | 0.20 | |
| C20:4n6 ARACHIDONIC | 0.61 | 0.70 | 0.6 |
| C20:3n3 Homo-γ-LINOLENIC | | | |
| C20:4n3 | | | |
| C20:5n3 EPA | 27.35 | 31.90 | 12.9 |
| C22:0 BEHENIC | | | |
| C22:1 ERUCIC | 1.22 | 1.50 | |
| C22:2n6 | | | |
| C22:4n6 | | | |
| C22:5n6 METHYL DPA | | | |
| C22:5n3 DPA | | 1.00 | |
| C22:6n3 DHA | 24.9 | 14.20 | 32.1 |
| C24:0 LIGNOCERIC | | | |
| C24:1 NERVONIC | | | |
| Total | 100.0 | 100 | 100 |

Compared to phospholipids existing in the market today, the extract phospholipids:

(a) achieve a superior profile;
(b) have the highest quantities of polyunsaturated fatty acids;
(c) have the highest quantities of DHA;
(d) are the only phospholipids that contain EPA; and
(e) are the only phospholipids that contain a combination of EPA and DHA on the same molecule.

PL=phospholipid
FA=fatty acid
PC=phosphatidylcholine
PE=phosphatidylethanolamine Free fatty acids are present in the extract in an amount of at least 4% w/w and preferably at least 5% w/w. Polyunsaturated fatty acids, in particular omega-3 fatty acids, preferably make up at least 15% w/w, more preferably at least 40% w/w, and even more preferably at least 45% w/w, of the total lipids in the extract. DHA and EPA are generally the largest component of the fatty acids and preferably account for at least 32% w/w, more preferably at least 35% or 37%, of the total lipid content of the extract.

Table 3 below details the fatty acid composition of the total lipids of the extract.

TABLE 3

Fatty acid composition of total lipids of the extract

| Sample Fatty Acid Composition | % |
|---|---|
| C14:0 | ≥3.00 |
| C14:1 | ≥0.01 |
| C15:0 | ≥0.3 |
| C16:0 | ≥20.00 |
| C16:1 | ≥3.25 |
| C18:0 | ≥1.00 |
| C18:1 | ≥10.00 |
| C18:2n6 | ≥2.00 |
| C18:3n6 GLA | ≥0.04 |
| C18:3n3 ALA | ≥0.01 |
| C18:4n3 | ≥1.50 |
| C20:0 | ≥0.05 |
| C20:1 | ≥1.00 |
| C20:2n6 | ≥0.05 |
| C20:3n6 | ≥0.05 |
| C20:4n6 | ≤0.50 |
| C20:3n3 | ≥0.01 |
| C20:4n3 | ≥0.20 |
| C20:5n3 EPA | ≥25.00 |
| C22:0 | ≥0.01 |
| C22:1 | ≥1.50 |
| C22:2n6 | ≥0.03 |
| C22:4n6 | ≥0.01 |
| C22:5n6 | ≥0.01 |
| C22:5n3 DPA | ≥0.50 |
| C22:6n3 DHA | ≥10.00 |
| C24:0 | ≥0.01 |
| C24:1 | ≥0.05 |

Table 4 below also details the fatty acid composition of the total lipids of the extract.

TABLE 4

Fatty acid composition of total lipids of the extract

| Saturated (g/100 g lipid) | ≥22.00 |
|---|---|
| Monounsaturated (g/100 g lipid) | ≥11.00 |
| Polyunsaturated (g/100 g lipid) | ≥35.00 |
| Omega-3 (g/100 g lipid) | ≥30.00 |
| Omega-6 (g/100 g lipid) | ≥1.00 |

Antioxidants present in the extract may include vitamin A (for example, all-trans retinol), vitamin E (for example, alpha-tocopherol), beta-carotene, astaxanthin (mainly esterified but non-esterified may be present), canthaxanthin and/or flavonoids. Antioxidants are preferably present in the extract in an amount of at least 20 and preferably at least 200 mg/100 ml.

Table 5 below details the lipids and other compounds (non-metal) of the extract.

TABLE 5

Lipid composition, vitamins A and E, pigments and flavonoids of the extract

| Monoglycerides (MG) (g/100 g sample) | ≥0.7 |
|---|---|
| Triglycerides (TG) (g/100 g sample) | ≥3.00 |
| Free Fatty Acids (FFA) (g/100 g sample) | ≥5.00 |
| Cholesterol (g/100 g sample) | ≤2.00 |
| Total Phospholipids (PL) (g/100 g sample) | ≥40.00 |
| Phosphatidyl Ethanolamine (PE) (g/100 g sample) | ≥2.50 |
| Phosphatidyl Inositol (PI) (g/100 g sample) | ≥0.20 |
| Phosphatidyl Serine (PS) (g/100 g sample) | ≥0.20 |
| Phosphatidyl Choline (PC) (g/100 g sample) | ≥35.00 |
| Sphingomyelin (g/100 g sample) | ≥0.50 |
| Vitamin A (μg/100 ml) | ≥1,400 |
| Vitamin E (μg/100 ml) | ≥15 |
| Beta-Carotene (μg/100 ml) | ≥1,600 |
| Astaxanthin (mg/100 ml) | ≥10 |
| Canthaxanthin (mg/100 ml) | ≥10 |
| Flavonoid (mg/100 ml) | ≥7.0 |

The metals present in the extract are preferably zinc and selenium. Zinc is preferably present in an amount of at least 0.05 mg/100 g of extract while selenium is generally present in an amount of less than 3 mg/100 g of extract.

Table 6 below details the metals content of the extract.

TABLE 6

Metal composition and solvent residue of the extract mixture

| Zinc (mg/100 g) | >0.1 |
|---|---|
| Selenium (mg/100 g) | <2 |
| Solvent residue | <25 ppm |

Table 7 below details the physiochemical characteristics of the extract.

TABLE 7

Physiochemical characteristics of the extract

| Color | Red |
|---|---|
| Viscosity (cPs) | <1300 |
| Odor | Fish |

Extraction of the phospholipid composition from the biomass is generally carried out by a method similar to the one described in commonly owned PCT publication number WO 00/23546, published on Apr. 27, 2000, the disclosure of which is incorporated herein by reference. The extraction is generally carried out by successive acetone and alcohol treatments. For the extraction of the instant application, the preferred treatment involves the use of >60% acetone in the first extraction followed by extraction with a mixture of organic solvents at 65-95%/45-50% preferably acetone, ethyl acetate/ethanol mixture. The most preferred extraction solvent system is 100% acetone in the first extraction followed with a 95%/5% ethyl acetate/ethanol mixture. However, other ketones can also be used in combination with or in place of acetone. The alcohol can be other than ethanol, e.g., isopropanol or t-butanol. The acetate may also vary. Further, the ratio of alcohol to acetate may vary widely from 100:0 to 0:100. The procedure produces two successive lipid fractions and a dry residue enriched in protein, including active enzymes.

Preferably, freshly harvested and finely divided marine and aquatic animal material is subjected to acetone extraction, for at least about two hours and preferably overnight. However, extraction time is not critical to the yield of lipid extracted. Particle sizes of comminuted crustacean less than 5 mm are preferred. The extraction is preferably conducted under an inert atmosphere and at a temperature of about 5 degrees Celsius or less. The mixture may be agitated during extraction and a volume ratio of about 6:1 of acetone to biomass is generally most preferred.

The solubilized lipid fraction is separated from the solid starting material by known techniques, for example, by filtration, centrifugation or sedimentation. Filtration is preferred. The residue is optionally washed with acetone to recover more lipid and the acetone removed by flash evaporation or spray drying. Water residue is allowed to separate from the lipid extract at low temperature.

The solid residue left on the filter from the initial extraction is suspended and extracted with 95/5 ethyl acetate/ethanol, preferably two volumes (original volume of material). The filtrate is evaporated yielding a second fraction of lipids. Extraction period is not critical although it is preferred to extract for about 30 minutes at a temperature below about 5 degrees Celsius.

Each phospholipid is subdivided into multiple categories depending on the fatty acids that are attached to the molecule. The biological activity, bioavailability as well as the value of phospholipids is determined by the purity and the source:

(a) Purity:
  (i) Optimal purity of the phospholipid or flavonoid of the invention is at least 99% by weight. The purity of the phospholipid or flavonoid after extraction from the krill may vary, but will normally be in the range of at least 90% to 100% of the/or mixture of phospholipid compound(s). Usually, the purity will be at least 95%. Preferably, the purity will be at least 96%, 97% or 98%. More preferably, the purity will be at least 99.5%. Most preferably, the purity will be at least 99.9%. By "purity" is meant that the phospholipid or flavonoid of the invention is isolated from other phospholipids, flavonoids, or components of the extract, to the weight percent specified. Isolation may be performed by e.g. HPLC. For example, a phospholipid that is 99% pure, contains less than 1% by weight of any material other than the specified phospholipid.
  (ii) Higher bioavailability and efficacy is achieved with higher purity.
  (iii) Phospholipid market value is directly analogous to the purity achieved for the final product.
(b) Source and fatty acid content:
  (i) The types of fatty acids attached to the phospholipid is widely dependent upon the source.
  (ii) Plant source phospholipids contain mainly palmitic acid (16:0), stearic acid (18:0), vaccenic acid (18:1), linoleic acid (18:2) or alpha-linoleic acid (18:3).
  (iii) Animal source phospholipids contain a higher percentage of longer-chain fatty acids with higher degree of unsaturation like homo-gamma-linoleic acid (20:3), arachidonic acid (20:4), behenic acid (22:0) and docosahexanoic acid-DHA (22:6).
  (iv) Neptune Krill Oil™ (the present invention) phospholipids contain high quantities of eicosapentanoic acid—EPA (20:5) and docosahexanoic acid—DHA (22:6). Their fatty acid profile closely resembles that of human brain phospholipids.
  (v) The efficacy in human health and the value of phospholipids increases directly analogous to the length of the fatty acid chain and the degree of unsaturation. Therefore, phospholipids with more polyunsaturated fatty acids attached to them are more efficacious and of higher value.
  (vi) Arachidonic acid, although polyunsaturated, has been proven to predispose to inflammatory disease. Hence, moderate quantities are preferred.
  (vii) DHA and EPA are the two most active polyunsaturated fatty acids in the human body, contributing to all health benefits associated with omega-3 fatty acids.
  (viii) The highest quantities of polyunsaturated fatty acids contained in the phospholipids in the market today are:
    a. Arachidonic acid: 30.1%
    b. Homo-gamma-linolenic acid: 9.0%
    c. DHA: 8.4%

4. Pharmaceutical, Nutraceutical and Cosmetic Compositions

The phospholipid extract of the present invention may be used with or without other additives. Preferably, no other additives are used. However, if other additives are used, pharmaceutical or nutraceutical formulations may be made by methods known in the art. For example, the compositions of the present invention may be formulated in a conventional manner using one or more pharmaceutically or nutraceutically acceptable carriers. Thus, the extract may be formulated for oral administration. For oral administration, the pharmaceutical or nutraceutical compositions may take the form of, for example, tablets or capsules prepared by conventional means with pharmaceutically or nutraceutically acceptable excipients such as binding agents (e.g., pregelatinised maize starch, polyvinylpyrrolidone or hydroxypropyl methylcellulose); filters (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically or nutraceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

When the phospholipid extract of the inventions is used as a nutraceutical, it can be in the form of foods, beverages, energy bars, sports drinks, supplements or other forms all as are known in the art.

As noted above, the phospholipid extract of the invention is also useful in cosmetic preparations, e.g., moisturizing creams, sun-block products and other topical cosmetic products as known in the art.

The phospholipid extract of the present invention may be used in the treatment or prevention of a variety of disease states including: liver disease; chronic hepatitis; steatosis;

liver fibrosis; alcoholism; malnutrition; chronic parenteral nutrition; phospholipid deficiency; lipid peroxidation; disarrhythmia of cell regeneration; destabilization of cell membranes; coronary artery disease caused by hypercholesterolemia; high blood pressure; menopausal or post-menopausal conditions; cancer, e.g., skin cancer; hypertension; aging; benign prostatic hyperplasia; kidney disease; edema; skin diseases; gastrointestinal diseases; peripheral vascular system diseases (e.g. leg ulcers); pregnancy toxemia; and neurodegenerative and psychiatric diseases (e.g. Parkinson's, Alzheimer's, autism, attention deficit disorder, learning disorders, mood disorders, bipolar depression, multiple sclerosis, muscular dystrophy).

The extracts are also useful for targeting tumors and can be used in conjunction with radioisotopes for diagnosing central nervous system tumors. The extract can also be used to reduce local fat deposits and reducing visible cellulite. The extract can also be used in aesthetics such as breast enlargement by acting on the lobular tissue of the breast and by increasing hydration of the breast.

As noted above, the present invention provides novel phospholipids derived from a marine or aquatic biomass. The novel phospholipids have the general formula (I):

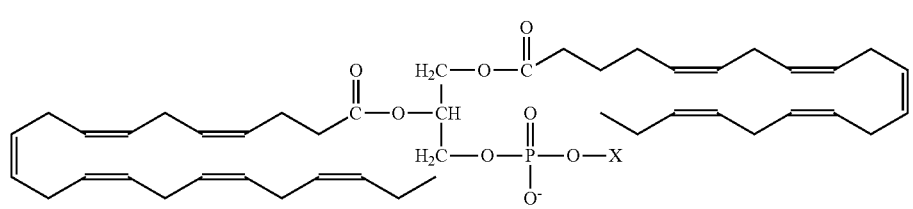

wherein X represents a moiety normally found in phospholipids, e.g., —CH$_2$CH$_2$N(CH$_3$)$_3$, CH$_2$CH$_2$NH$_3$ or

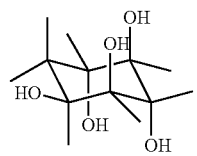

for phophatidylcholine, phosphatidylethanolamine or phosphatidylinositol, respectively.

The left hand acid residue is derived from docosahexanoic acid (DHA) [C22:6n3]. The right hand acid residue is derived from eicosapentaenoic acid (EPA) [C20:5n3].

These novel phospholipids have all of the uses noted above for phospholipids in pharmaceutical, nutraceutical and cosmetic compositions.

As noted above, the present invention also provides a novel flavonoid compound derived from a marine or aquatic biomass. The novel flavonoid compound has the formula (II):

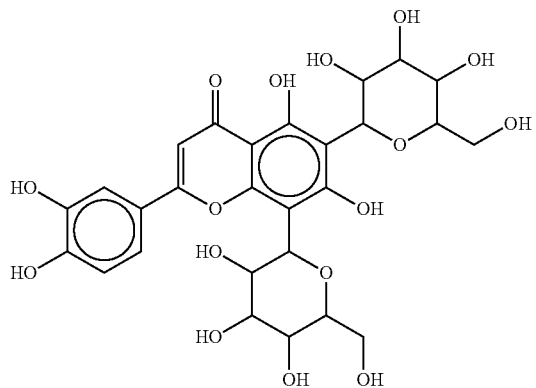

The novel flavonoid is an antioxidant and thus is useful in the pharmaceutical, nutraceutical and cosmetic compositions of the invention.

As used herein and in the claims, where the term "about" is used with a numerical value, the numerical value may vary by at least ±50%. Preferably, the variation will be ±40% or ±30% and more preferably ±20% or ±10%. Even more preferred variations are in the range ±5%, ±4%, ±3% or ±2%. Most preferably, the variation is in the range of ±1%.

The invention is further illustrated by the following non-limiting examples.

The extraction of the phospholipids for Example 1 was as described above for krill extractions.

EXAMPLES

Materials and Methods

For analysis of lipids, samples were dissolved in solvent and standards were added. Lipid classes were isolated using silica gel and quantified. Fatty acid composition of total lipids and individual phospholipids was determined by gas chromatography. Pigments were measured by reversed phase high performance liquid chromatography.

Example 1

This example illustrates the isolation and molecular characterization of the phospholipids from the extract.

Sample #804 Molecular Species Determination

The sample contains large amounts of phospholipids, mainly:

PC (438.48 mg/g lipid)
PE (183.15 mg/g lipid)

Preliminary results were obtained only for these two phospholipid fractions.

METHODS

Separation of Main Phospholipid Fractions

To obtain large quantities of PC and PE, separation was done by Thin Layer Chromatography (TLC) and bands identity was confirmed by HPLC.

Diacylglycerol Formation

Both fractions (PC and PE) were incubated with phospholipase C, the enzyme which removes choline phosphate from PC and ethanolamine phosphate from PE. The remaining diacylglycerols were extracted with ethyl ether.

Benzoate Derivatization

Each mixture of diacylglycerols needed to be derivatized (using benzoic anhydride and 4-dimethyl-aminopyridine) to make further separation possible. In a parallel experiment, derivatization was done for three standard authentic diacylglycerols, dilinolein, diolein and dipalmitin.

Subclass Separation

A preliminary separation of diacylglycerols derivatives into subclasses was done by TLC. Diacylglycerol derivatives obtained from PC and from PE separated into two major bands (#3 and #4). Additional bands #2 were also visible very close to the start. Only bands #3 and #4 were processed further because their localization corresponded to the localization of main band #2 obtained for a mixture of standards (benzoate derivatives of dilinolein, diolein and dipalmitin).

Example TLC Plate Separation

| | | |
|---|---|---|
| #3 | | |
| #2 | #4 (Rf = 0.37) | #4 (Rf = 0.37) |
| | #3 (Rf = 0.25) | #3 (Rf = 0.25) |
| | #2 | #2 |
| Start | Start | Start |
| Std Mix | PC | PE |

HPLC Fractionation

Bands #3 and #4 obtained for PC and PE were eluted and further separated into individual diacylglyercol species by HPLC. To confirm a number of peaks for the subsequent GC analysis, each peak was collected and separately re-run on HPLC.

Number of Confirmed Peaks

For PC band #3, nine peaks were identified and confirmed.

For PC band #4, nine peaks were identified and confirmed.

For PE band #3, eight peaks were identified and confirmed.

For PE band #4, eight peaks were identified and confirmed.

Figure 1:
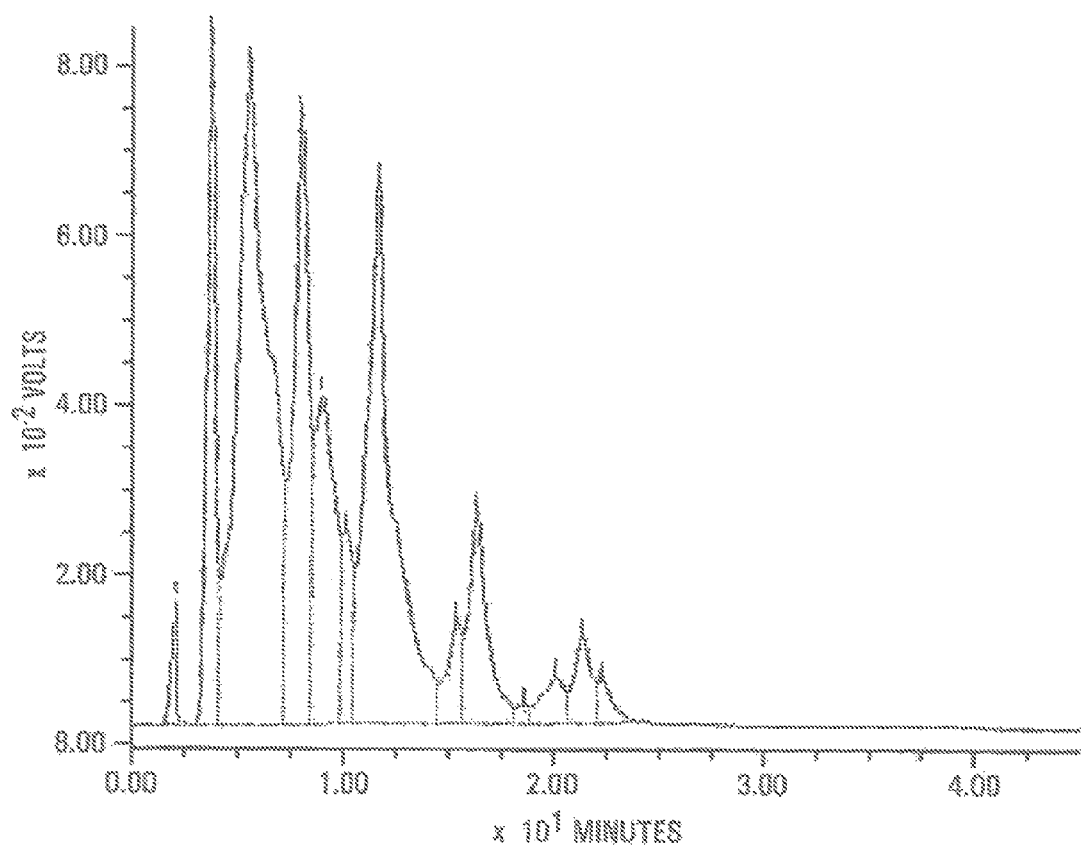
FIGS. 1 to 3 are chromatograms of the product of Example 1.

See FIG. 1.

Hydrolysis, Methyl Ester Derivatization and GC Analysis

For both PC and PE, all confirmed peaks obtained from HPLC separation of band #3 were hydrolized and fatty acid profiles were determined by GC after conversion into methyl esters. Peak identity was assessed by mass spectrometry. Fatty acid profiles were compared to those obtained for intact PC and PE fractions subjected to hydrolysis and methylation.

Results

The peak surface areas calculated for fatty acid molecular species in selected fractions are summarized in Table 8. The peak fatty acid areas for intact PC and PE fraction are in Table 9. The representative Gas Chromatography profiles for an individual fraction and for intact phospholipid (PC) are presented in Table 10.

The Gas Chromatography profiles obtained for individual peaks were only partly consistent with profiles obtained for intact PC. They contained only 5-6 major peaks while Gas Chromatography profiles of intact phospholipids consist of much higher number of peaks. Among the 5-6 peaks consistently found in molecular species profiles, only two had identity confirmed by mass spectrometry (C16:0 and C18:0). Among the remaining three peaks, one did not correspond to any fatty acid and two had retention times identical to those of authentic omega-3 fatty acids, EPA and DHA.

The C16:0 peak was prominent in all individual molecular species profiles and was also prominent in the intact phospholipid fractions. For the C18:0 peak, its proportions found in individual peaks were relatively high. Oleic acid (C18:1) was found at high levels in both PC and PE fatty acid profile.

TABLE 8

Molecular species peak areas obtained for selected fractions.

| Fraction | C16:0 | C18:0 | EPA | RT 48.33 | DHA |
|---|---|---|---|---|---|
| PC band #3 F1 | 205.27 | 57.79 | 42.76 | 103.83 | 62.07 |
| PC band #3 F2 | 21.39 | 8.87 | 0 | 71.96 | 7.11 |
| PC band #3 F3 | 58.74 | 17.70 | 0 | 45.64 | 14.75 |
| PC band #3 F4 | 93.41 | 9.72 | 0 | 44.31 | 9.19 |
| PC band #3 F5 | 19.87 | 9.67 | 4.56 | 46.89 | 3.96 |
| PC band #3 F6 | 15.26 | 10.34 | 12.45 | 59.86 | 14.29 |
| PC band #3 F7 | 28.32 | 10.93 | 30.70 | 56.83 | 25.12 |
| PC band #3 F8 | 6.39 | 4.49 | 0 | 84.24 | 11.89 |
| PC band #3 F9 | 14.65 | 8.21 | 8.60 | 58.95 | 28.22 |
| PE band #3 F2 | 4.50 | 10.79 | 0 | 77.68 | 9.19 |
| PE band #3 F3 | 26.85 | 22.14 | 14.45 | 49.62 | 21.76 |
| PE band #3 F4 | 13.08 | 22.45 | 28.70 | 62.11 | 29.43 |
| PE band #3 F5 | 22.42 | 20.34 | 11.06 | 100.79 | 30.61 |
| PE band #3 F6 | 3.05 | 6.13 | 4.93 | 54.88 | 7.28 |

TABLE 9

Selected fatty acid peak areas of intact PC and PE

| | C16:0 | C18:0 | C18:1 | EPA | Un-identified | DHA |
|---|---|---|---|---|---|---|
| Retention time | 15.80 | 21.66 | 22.36 + 22.63 | 39.68 | 48.34 | 53.59 |

TABLE 9-continued

Selected fatty acid peak areas of intact PC and PE

|    | C16:0   | C18:0 | C18:1  | EPA    | Un-identified | DHA    |
|----|---------|-------|--------|--------|---------------|--------|
| PC | 1141.36 | 35.75 | 257.99 | 642.50 | 68.61         | 192.22 |
| PE | 166.43  | 20.45 | 87.75  | 59.77  | 110.27        | 109.63 |

Figure 2:
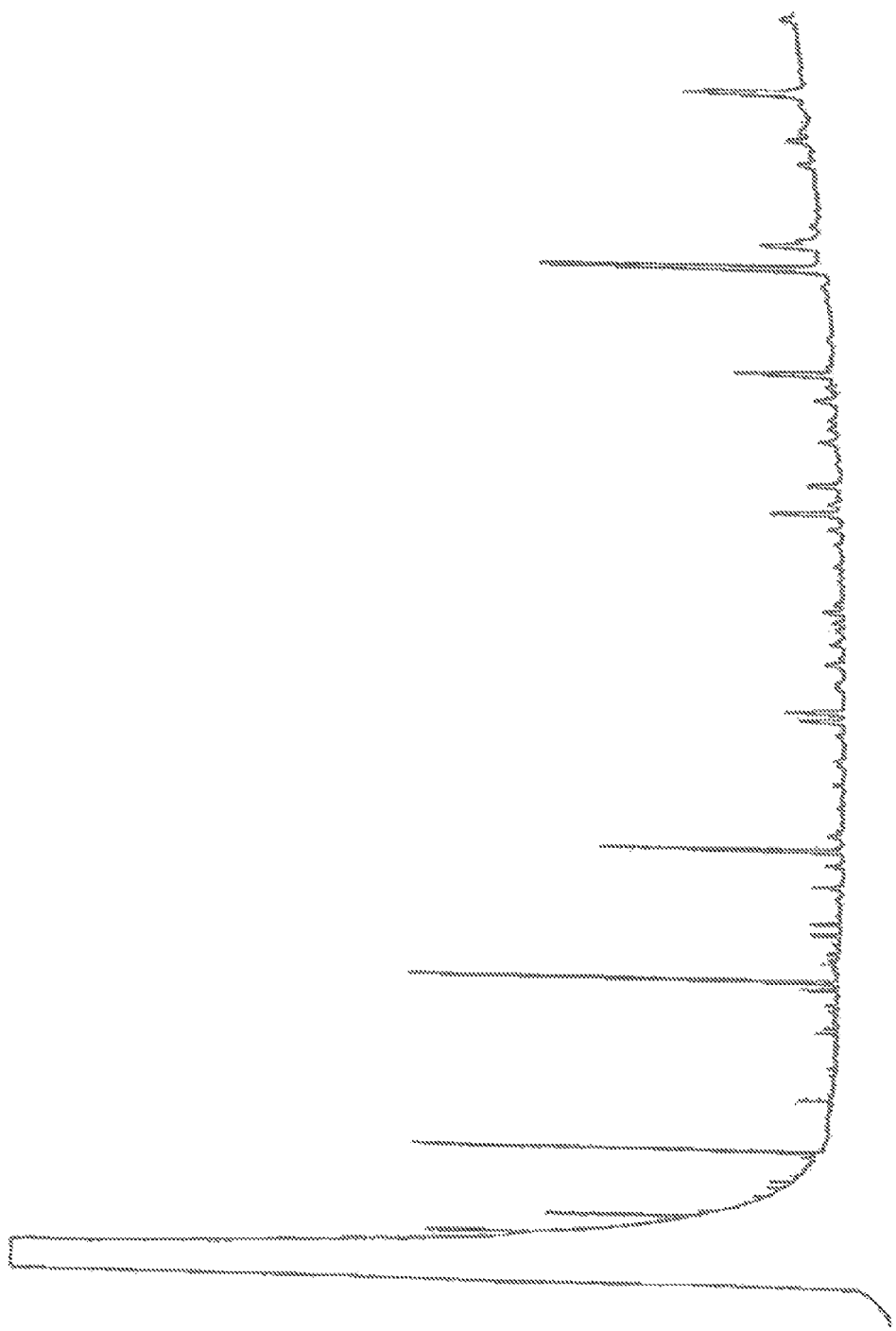

See FIG. 2

TABLE 10

The representative GC profiles for an individual fraction and for intact phospholipid (PE)

| CH | PKNO | TIME   | AREA     | HEIGHT  | MK | IDNO | CONC    |
|----|------|--------|----------|---------|----|------|---------|
| 1  | 5    | 0.826  | 17654310 | 1368301 | E  |      | 21.8397 |
|    | 13   | 2.637  | 11027760 | 1352920 | E  |      | 13.6422 |
|    | 14   | 2.916  | 2167386  | 203115  | E  |      | 2.6812  |
|    | 15   | 3.15   | 597812   | 87264   | V  |      | 0.7395  |
|    | 22   | 4.408  | 667991   | 60799   | V  |      | 0.8264  |
|    | 29   | 7.063  | 7293939  | 290768  |    |      | 9.0231  |
|    | 30   | 8.397  | 144489   | 13997   |    |      | 0.1787  |
|    | 32   | 9.933  | 32467398 | 1384059 | E  |      | 40.1646 |
|    | 33   | 10.252 | 8166303  | 661493  | V  |      | 10.1023 |
|    | 43   | 14.451 | 348072   | 20030   |    |      | 0.4306  |
|    | 44   | 14.813 | 102126   | 9975    |    |      | 0.1263  |
|    | 45   | 15.12  | 198366   | 21561   |    |      | 0.2454  |
| TOTAL |   |        | 80835952 | 5474282 |    |      | 100     |

Figure 3:
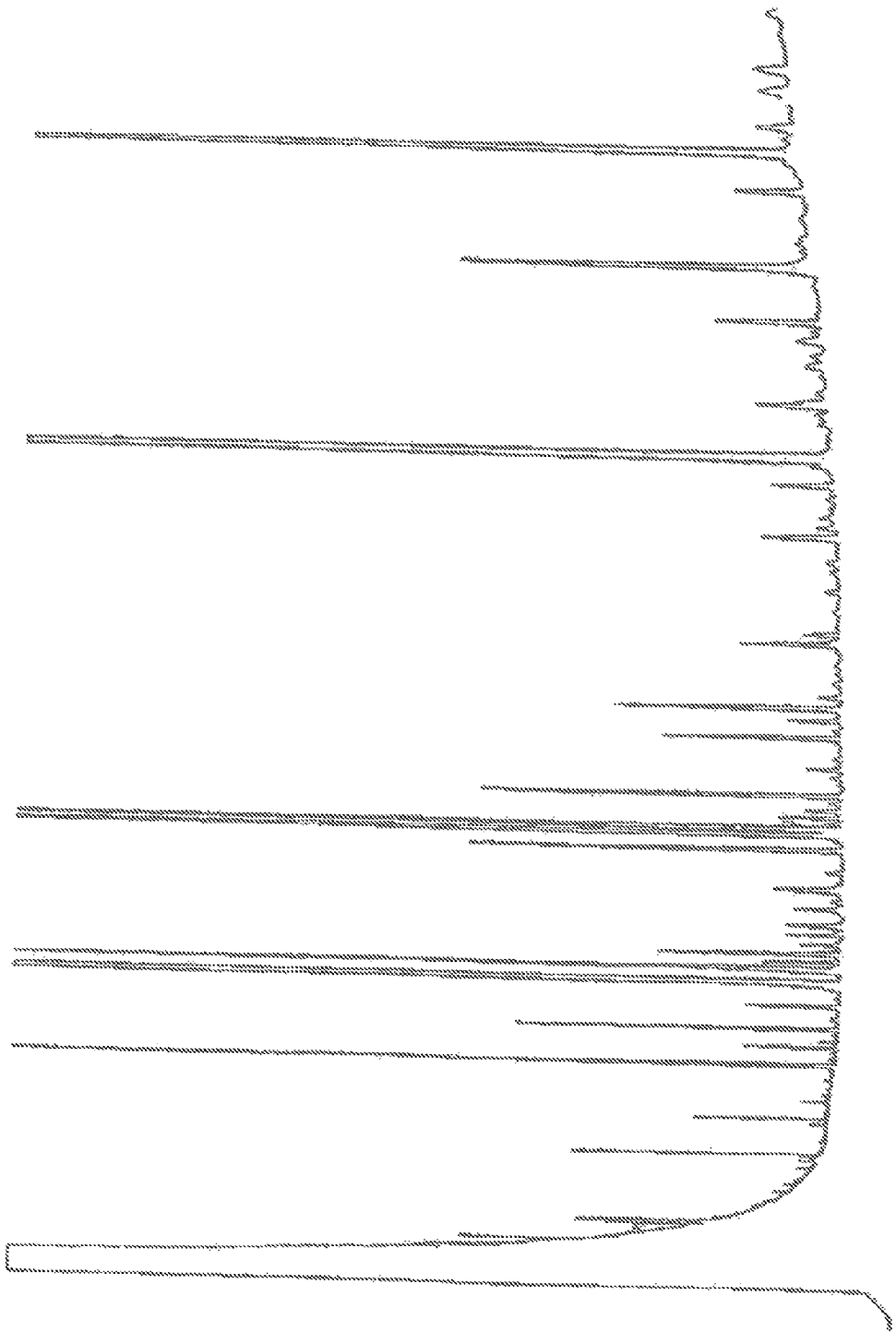
Figure 4:
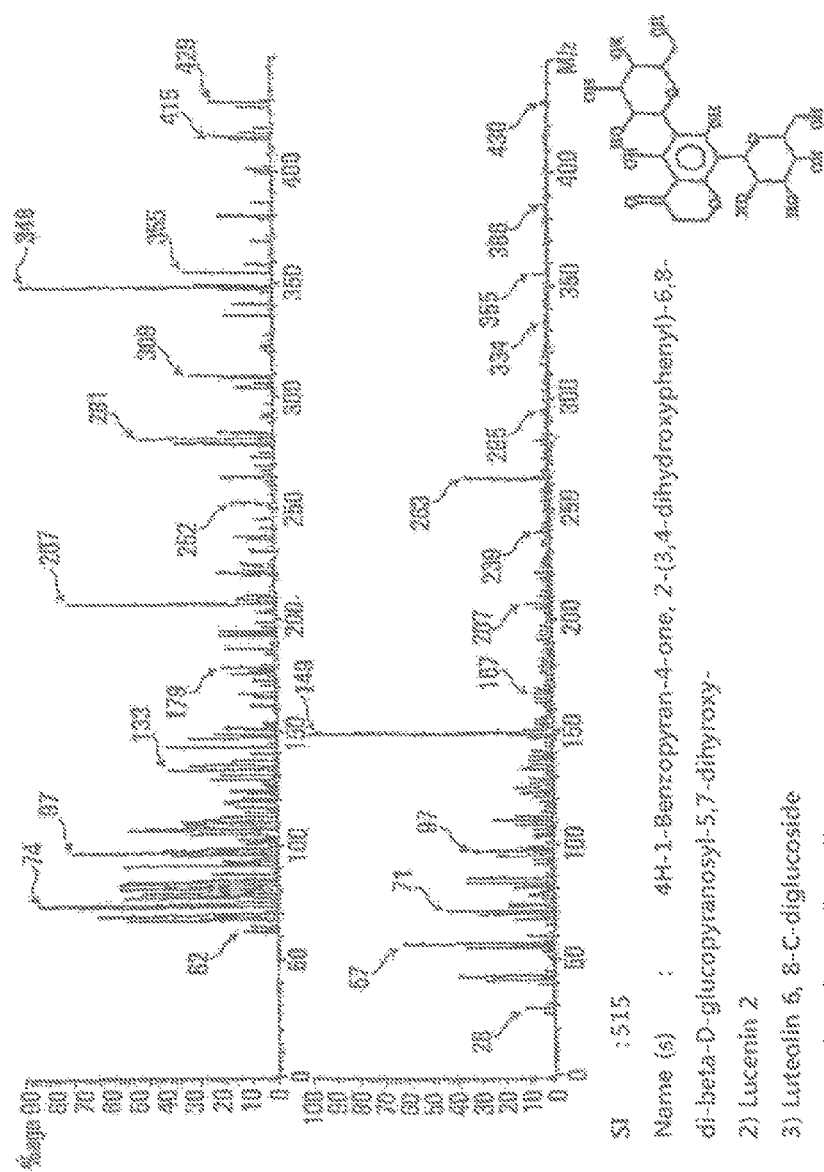
FIG. 4 is a mass spectrograph for characterizing the novel flavonoid compound (II).

See FIG. 3

Example 2

UVB-Induced Skin Cancer
Objectives
To evaluate the photoprotective potential of krill extract against UVB-induced skin cancer.
Study Design
  Randomized control trial
  Statistical significance p<0.05
Study Phase
  Pre-clinical
Experimental Animals
  Type: Nude Mice
  Strain: C57BL6 Nude Congenic Mice—B6NU-T (heterozygotes) (Preference of specific type because of proven susceptibility to skin cancer).
Study Protocol
  Number of nude mice=96
  Randomization groups: 48 placebo: 16 per os
    16 local application
    16 per os and local application
  48 krill extract: 16 per os
    16 local application
    16 per os and local application
In order to establish efficacy of krill extract for the prevention of skin cancer, the test was conducted as a randomized double blind controlled trial (both the pathologist and the research assistant were blind). Half of the mice were treated orally or topically or both with extract containing 100% by weight of krill extract and the other half underwent the same method of treatment with a placebo. The groups were divided as follows:
  Nutrition: Week 1: fat-free chow
  Week 2-20: according to group Experimental Design:
  The mice were divided in six groups as follows:
  Group A: fat-free chow with supplementation of soy extract (20% of total calories)
  Group B: fat-free chow (100% of calories)+local application of soy extract 2 times per day
  Group C: fat-free chow with supplementation of soy extract (20% of total calories)+local application of soy extract 2 times per day
  Group D: fat-free chow with supplementation of krill extract (20% of total calories)
  Group E: fat-free chow (100% of calories)+local application of krill extract 2 times per day
  Group F: fat-free chow with supplementation of krill extract (20% of total calories)+local application of krill extract 2 times per day
  Week 2-20: UVB radiation using a fluorescent test lamp, emission spectrum 270-400 nm.
  Week 3-20: liquid from blisters formed is examined for PGE2 levels
  Week 3-20: mice are anaesthetized with ether and sacrificed when malignant tumours have formed or at the end of the 20 weeks.
  Skin is examined by pathologist for signs of carcinogenesis.
  The results are shown in the following Table 11.

TABLE 11

|             | Frequency of cancer        |                         |
|-------------|----------------------------|-------------------------|
| Application | Krill Oil Frequency %      | Placebo Frequency %     |
| Oral        | 13                         | 69.3                    |
| Topical     | 0                          | 63.8                    |
| Oral & Topical | 0                       | 37.5                    |

In conclusion, the results of the present study demonstrate that both oral and topical krill extract may be effectively used for the protection of skin against the harmful effects of UVB radiation including skin cancer.

Example 3

This example illustrates the use of the present krill extract in improving dyslexia and abnormal motor function in a 7 year old girl.

2 g per day of the krill extract were given to a 7 year old girl suffering from dyslexia and abnormal motor function. After 1.5 months, she showed:

Increased learning ability (blind observation by psychologist)
Improved motor function (moderate ice skating)
Improved social skills
Improved speech Accordingly, the krill extract has beneficial neurological properties.

All publications cited in this specification are herein incorporated by reference as if each individual publication were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

1. Lisa Colodny, Pharm D. and Ronald L. Hoffman, M. D. Altern Med Rev 1998; 3(6): 432-447.
2. Vandal R. Role of inositol in the treatment of psychiatric disorders. CNS Drugs 1997; 7:6-16.
3. Gill D L, Ghosh T K, Mullaney J M. Calcium signaling mechanisms in endoplasmic reticulum activated by inositol 1,4,5 triphosphate and GTP. Cell Calcium 1989; 10:363-374.
4. Parthasarathy L, Vadnal R, Parthasarathy R, et al. Biochemical and molecular properties of lithium-sensitive myo-inositol monophosphatase. Life Sci 1994; 54:1127-1142.
5. Kitamura H, Yamauchi A, Sugiura T, et al. Inhibition of myo-inositol transport causes acute renal failure with selective medullary injury in the rat. Kidney Int 1998; 53:146-153.
6. Barkai A, Dunner D, Gross H, et al. Reduced myo-inositol levels in cerebrospinal fluid from patients with affectiv disorder. Biol Psychiatry 1978; 13:65-72.
7. Levine J, Rapaport A, Lev L, et al. Inositol treatment raises CSF inositol levels. Brain Research 1993; 627: 168-169.
8. Levine J. Controlled trials of inositol in psychiatry. Eur Neuropsychopharmacol 1997; 7:147-155.
9. Cohen H, Kotler M, Kaplan Z, et al. Inositol has behavioral effects with adaptation after chronic administration. J Neural Transm 1997; 104:299-305.
10. Levine J, Barak Y, Gonzalves M, et al. Double-blind, controlled trial of inositol treatment of depression. Am J Psychiatry 1995; 152:792-794.
11. Levine J, Barak Y, Kofman O, et al. Follow-up and relapse of an inositol study of depression. Isr J Psychiatry Relat Sci 1995; 32:14-21.
12. Benjamin J, Levine J, Fux M, et al. Double-blind, placebo-controlled, crossover trial of inositol treatment for panic disorder. Am J Psychiatry 1995; 15:1084-1086.
13. Birchall J, Chappell J. Aluminum, chemical physiology, and Alzheimer's disease. Lancet 1988; 29: 1008-1010.
14. Cheng D, Ren H, Tang X. Huperzine A. A novel promising acetylcholinesterase inhibitor. Neuroreport 1996; 8:97-101.
15. Kawakami Y, Inoue A, Kawai T, et al. The rationale for E2020 as a potent acetylcholinesterase inhibitor. Bioorg Med Chem 1996; 4:1429-1446.
16. Knopman D, Schneider L, Davis K, et al. Long term tacrine (Cognex) treatment: effects on nursing home placement and mortality, tacrine study group. Neurology 1996; 47:166-167.
17. Mohr E, Nair N, Sampson M, et al. Treatment of Alzheimer's disease with sabeluzole: functional and structural correlates. Clin Neuropharmacol 1997; 20:338-345.
18. Rogers S, Friedhoff L. The efficacy and safety of donepezil in patients with Alzheimer's disease: results of a US multicentre, randomized, double-blind, placebo-controlled trial. The donepezil study group. Dementia 1996; 7:293-303.
19. Schneider L, Farlow M, Pogoda J. Potential role for estrogen replacement in the treatment of Alzheimer's dementia. Am J Med 1997; 103:46S-50S.
20. Van Dyck C, Lin C, Robinson R, et al. The acetylcholine releaser linopiridine increases pariental regional cerebral blood flow in Alzheimer's disease. Psychopharmacology 1997; 132:217-226.
21. Barak Y, Levine J, Glasman A, et al. Inositol treatment of Alzheimer's disease: a double blind, cross-over placebo controlled trial. Prog Neuropsychopharmacol Biol Psychiatry 1996; 20:729-735.
22. Michael D. Seidman, M D., FACS Polyunsaturated Phosphatidylcholine in NT Factor™ Improves Mitochondrial Function, Auditory Sensitivity and May Slow Some Aspects of the Aging Processes. Anti-aging Medical News, winter 2001-01.
23. Imperato A, Ramacci M T, Angelucci L. Acetyl L-carnitine enhances acetylcholine release in the striatum and hippocampus of awake freely moving rats. Neuroscience letters. 1989: 107(1-3): 251-255.
24. Ghirardi O, Milano S, Ramacci M T, Angelucci L. Effects of acetyl L-carnitine chronic treatment on discrimination models in aged rats. Physiol. Behav. 1988; 44(6): 769-773.
25. Caprioli A, Ghirardi O, Ramacci M T, Angelucci L. Age-dependent deficits in radial maze performance in the rat: effect of chronic treatment with acetyl L-carnitine. Prog. in Neuropsychopharmacol. Biol. Psychiatr. 1990; 14(3):3 59-369.

Bast A and Haenen GRMM. Interlay between lipoic acid and glutathione in the protection against microsomal lipid peroxidation. Biochem. Biophys. Acta. 1988; 963: 558-561.

26. Suzuki Y J, Aggarwal B, Packer L. Aipha-lipoic acid is a potent inhibitor of NFKb activation in human Tcells. Biochem. Biophys. Res. Commun. 1992; 189: 1709-1715.
27. Kagan V E, Shvedova A, Serbinova E, Khan S, Swanson C, Poweel R, Packer L. Dihydrolipoic acid: A universal antioxidant both in the membrane and in the aqueous phase. Biochem Pharmacol. 1992; 44: 1637-1649.
28. Devasagayam T P, Subramanian M, Pradhan D S, Sies H. Chemical Biological Interactions. 1993; 86: 79-92.
29. Gadaleta M N, Petruzalla V, Daddabbo L, et al. Mitochondrial DNA transcription and translation in aged rat. Effect of acetyl-L-carnitine. Ann. N.Y. Acad. Sci. 1994; 717: 150-160.

30. Paradies G, Ruggiero F M, Petrosillo G, Gadaleta M N, Quaglieriello E. Carnitine-acylcarnitine translocase activity in cardiac mitochondria from aged rats: the effect of acetyl-L-carnitine. Mech. of aging and develop. 1995; 84(2):103-112.

31. Aureli T, Miccheli A, Ricciolini R, Di Cocco M, et al. Aging brain: effect of acetyl L-carnitine treatment on rat brain energy and phospholipid metabolism. A study by 3 1P and 1H NMR spectroscopy. Brain Research. 1990; 526(1) :108-112.

32. Sebinova E, Khwaja S, Reznick A Z, Packer L. Thioctic acid protects against ischemia-reperfusion injury in the isolated perfused Langendorif heart. Free Rad. Res. Commun. 1994; 17: 49-58.

33. Seidman M D, Khan M J, Bai U, Shirwany N, Quirk W S. Biologic Activity of Mitochondrial Metabolites on Aging and Age-Related Hearing Loss. Am. J. Otol. 2000; 21:161-167.

34. Hosokawa M., Shimatani T., Kanada T., Inoue Y., and Takahashi K. Conversation of Docosahexaenoic Acid-Containing Phosphatidylserine from Squid Skin Lecithin by Phospholipase D-Mediated Transphosphatidylation. J. Agric. Food Chem. 2000, 48, 4550-4554.

35. Henderson R. J., Bell M. V., Park M. T., Sargent J. R., and Falcon J. Lipid Composition of the Pineal Organ from Rainbow Trout. Lipids, 29(5), 311-317 (1994).

36. Bell M. V. and Dick J. R. Molecular Species Composition of the Major Diacyl Glycerophospholipids from Muscle, Liver, Retina, and Brain of Cod. Lipids, 26(8), 565-573 (1991).

37. Wiegand R. D. and Anderson R. E. Phospholipid Molecular Species of Frog Rod Outer Segment Membranes. Exp. Eye Res., 37(2), 157-173 (1983).

The invention claimed is:

1. A method for treating coronary artery disease caused by hypercholesterolemia comprising orally administering to a patient in need thereof an effective amount of a krill oil, the krill oil comprising a phospholipid of the general formula (I)

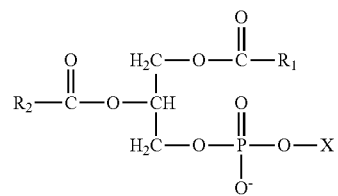

wherein:
R1 and R2, each together with the respective carboxyl groups to which each is attached, each independently represents a docosahexaenoic acid (DHA) or an eicosapentaenoic acid (EPA) residue,
X is —CH$_2$CH$_2$NH$_3$, —CH$_2$CH$_2$N(CH$_3$)$_3$ or

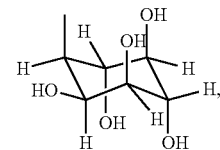

and
said composition is suitable for human consumption.

2. The method of claim 1, wherein said krill oil is contained in a capsule.

3. The method of claim 1, wherein said krill oil further comprises free fatty acids in an amount of about 5%, wherein about represents ±10%.

4. The method of claim 1, wherein said krill oil comprises polyunsaturated fatty acids in an amount of at least 15% w/w of the total lipids.

5. The method of claim 4, wherein said polyunsaturated fatty acids are omega-3 fatty acids.

6. The method of claim 1, wherein said krill oil comprises phospholipids in an amount of about 40% w/w, wherein about represents ±10%.

7. The method of claim 1, wherein said krill oil further comprises astaxanthin.

* * * * *